(12) United States Patent
Govari et al.

(10) Patent No.: US 12,048,479 B2
(45) Date of Patent: Jul. 30, 2024

(54) SURFACE MOUNTED ELECTRODE CATHETER

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 517 days.

(21) Appl. No.: 17/081,918

(22) Filed: Oct. 27, 2020

(65) Prior Publication Data

US 2022/0071693 A1 Mar. 10, 2022

Related U.S. Application Data

(60) Provisional application No. 63/076,614, filed on Sep. 10, 2020.

(51) Int. Cl.
*A61B 18/14* (2006.01)
*A61B 17/00* (2006.01)
(Continued)

(52) U.S. Cl.
CPC ............ *A61B 18/1492* (2013.01); *A61B 2017/00185* (2013.01); *A61B 2018/00077* (2013.01);
(Continued)

(58) Field of Classification Search
CPC ...... A61B 18/1492; A61B 2018/00577; A61B 2018/144; A61B 2018/00136;
(Continued)

(56) References Cited

U.S. PATENT DOCUMENTS 3,359,525 A 12/1967 Hubbach
4,699,147 A 10/1987 Chilson et al.
(Continued)

FOREIGN PATENT DOCUMENTS

CN 111248993 A 6/2020
CN 111248996 A 6/2020
(Continued)

OTHER PUBLICATIONS

Picwire.com, "Interconnect Solutions, 50 OHM RF Cable Solutions", https://picwire.com/Cables/50Ohm-Coax-Triax# :~:text=The%20temperature%20range%20for%20the,cable%20%2D55%2F%2B150%C2%B0 (Year: 2020).*
(Continued)

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

In one embodiment, a medical system includes a catheter configured to be inserted into a body part of a living subject, and including an elongated deflectable element including a distal end, a proximal coupler connected to the distal end, an expandable assembly comprising a plurality of flexible polymer circuit strips, the flexible polymer circuit strips having respective proximal ends connected to, and disposed circumferentially around, the proximal coupler, respective ones of the flexible polymer circuit strips including respective multiple strip electrodes, respective contact arrays disposed at the respective proximal ends, and respective multiple circuit traces electrically connecting the respective multiple strip electrodes with the respective contact arrays, and a plurality of surface mountable electrodes mounted on, and bulging over respective ones of the flexible polymer circuit strips.

21 Claims, 19 Drawing Sheets

(51) Int. Cl.
  *A61B 18/00* (2006.01)
  *A61B 18/12* (2006.01)
  *A61M 25/00* (2006.01)
(52) U.S. Cl.
  CPC ............. *A61B 2018/00136* (2013.01); *A61B 2018/00178* (2013.01); *A61B 2018/00267* (2013.01); *A61B 2018/00357* (2013.01); *A61B 2018/00577* (2013.01); *A61B 2018/00601* (2013.01); *A61B 2018/00613* (2013.01); *A61B 2018/00761* (2013.01); *A61B 2018/1253* (2013.01); *A61B 2018/126* (2013.01); *A61B 2018/144* (2013.01); *A61B 2018/1467* (2013.01); *A61B 2218/002* (2013.01); *A61M 2025/0079* (2013.01)
(58) Field of Classification Search
  CPC .......... A61B 2017/00185; A61B 2018/00077; A61B 2018/00178; A61B 2018/00267; A61B 2018/00357; A61B 2018/00601; A61B 2018/00613; A61B 2018/00761; A61B 2018/1253; A61B 2018/126; A61B 2018/1467; A61B 2218/002; A61M 2025/0079
  See application file for complete search history.

(56) References Cited

U.S. PATENT DOCUMENTS

| | | |
|---|---|---|
| 4,940,064 A | 7/1990 | Desai |
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,862,030 A * | 1/1999 | Watkins, Jr. ............ H02H 5/043 361/103 |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,944,022 A | 8/1999 | Nardella et al. |
| 5,968,040 A | 10/1999 | Swanson et al. |
| 5,983,126 A | 11/1999 | Wittkampf |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,569,162 B2 | 5/2003 | He et al. |
| 6,574,492 B1 | 6/2003 | Ben-Haim et al. |
| 6,582,429 B2 | 6/2003 | Krishnan et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,475,450 B2 | 7/2013 | Govari et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,044,232 B2 * | 6/2015 | Cheng ................. A61B 18/082 |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |

(56) References Cited

U.S. PATENT DOCUMENTS

| | | |
|---|---|---|
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0125772 A1 | 5/2008 | Stone et al. |
| 2008/0234564 A1 | 9/2008 | Beatty et al. |
| 2011/0118726 A1 | 5/2011 | De La Rama et al. |
| 2011/0137298 A1 | 6/2011 | Nguyen et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2012/0067640 A1 | 3/2012 | Moulin et al. |
| 2012/0271136 A1 | 10/2012 | Kordis et al. |
| 2013/0131661 A1 | 5/2013 | Jackson et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0282084 A1 | 10/2013 | Mathur et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276124 A1* | 9/2014 | Cholette ............. A61B 5/01 600/483 |
| 2014/0276712 A1 | 9/2014 | Mallin et al. |
| 2014/0276733 A1 | 9/2014 | Van Scoy et al. |
| 2014/0276789 A1 | 9/2014 | Dandler et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0157382 A1 | 6/2015 | Avitall et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2015/0366508 A1* | 12/2015 | Chou ............ A61B 5/287 600/467 |
| 2016/0073960 A1 | 3/2016 | Jung et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |

(56) References Cited

U.S. PATENT DOCUMENTS

| | | |
|---|---|---|
| 2017/0164858 A1 | 6/2017 | Basu |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0042674 A1 | 2/2018 | Mickelsen |
| 2018/0049803 A1 | 2/2018 | Solis |
| 2018/0056038 A1 | 3/2018 | Aujla |
| 2018/0085064 A1 | 3/2018 | Auerbach et al. |
| 2018/0092688 A1 | 4/2018 | Tegg |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0214202 A1 | 8/2018 | Howard et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0353238 A1 | 12/2018 | Schultz |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0282116 A1 | 9/2019 | Olson |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0107879 A1 | 4/2020 | Stewart et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2020/0398050 A1 | 12/2020 | Viswanathan et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1* | 4/2021 | Govari .................. A61B 5/036 |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altman et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |

(56) References Cited

U.S. PATENT DOCUMENTS

| | | | |
|---|---|---|---|
| 2021/0338319 | A1 | 11/2021 | Govari et al. |
| 2022/0304745 | A1 | 9/2022 | Olson |

FOREIGN PATENT DOCUMENTS

| | | | |
|---|---|---|---|
| CN | 111728693 | A | 10/2020 |
| EP | 0668740 | A1 | 8/1995 |
| EP | 0879613 | A2 | 11/1998 |
| EP | 0644738 | B1 | 3/2000 |
| EP | 0727183 | B1 | 11/2002 |
| EP | 0727184 | B1 | 12/2002 |
| EP | 2783651 | A1 | 10/2014 |
| EP | 2699151 | B1 | 11/2015 |
| EP | 2699152 | B1 | 11/2015 |
| EP | 2699153 | B1 | 12/2015 |
| EP | 2954868 | A1 | 12/2015 |
| EP | 2498706 | B1 | 4/2016 |
| EP | 2578173 | B1 | 6/2017 |
| EP | 3181082 | A1 | 6/2017 |
| EP | 3238645 | A1 | 11/2017 |
| EP | 2884931 | B1 | 1/2018 |
| EP | 2349440 | B1 | 8/2019 |
| EP | 3318211 | B1 | 12/2019 |
| EP | 3581135 | A1 | 12/2019 |
| EP | 2736434 | B1 | 2/2020 |
| EP | 3451962 | B1 | 3/2020 |
| EP | 3967253 | A2 | 3/2022 |
| EP | 3972510 | A1 | 3/2022 |
| EP | 3991681 | A1 | 5/2022 |
| WO | 9421167 | A1 | 9/1994 |
| WO | 9421169 | A1 | 9/1994 |
| WO | WO 1996/005768 | | 2/1996 |
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014/124231 | A1 | 8/2014 |
| WO | 2014/158708 | A1 | 10/2014 |
| WO | 2014176205 | A1 | 10/2014 |
| WO | 2016019760 | A1 | 2/2016 |
| WO | 2016044687 | A1 | 3/2016 |
| WO | 2016/075544 | A2 | 5/2016 |
| WO | 2016/130713 | A1 | 8/2016 |
| WO | 2018111600 | A1 | 6/2018 |
| WO | 2018191149 | A1 | 10/2018 |
| WO | 2019084442 | A1 | 5/2019 |
| WO | 2019143960 | A1 | 7/2019 |
| WO | 2019/177809 | A1 | 9/2019 |
| WO | 2020026217 | A1 | 2/2020 |
| WO | 2020206328 | A1 | 10/2020 |
| WO | 2020251857 | A1 | 12/2020 |

OTHER PUBLICATIONS

Partial European Search Report dated Jan. 26, 2022, from corresponding European Appl. No. 21195668.5.
Extended European Search Report dated Jun. 1, 2022, from corresponding European Appl. No. 21195668.5.
Extended European Search Report dated Dec. 2, 2022, from corresponding European Appl. No. 22183542.4.
Ron Robinette, "Swiss Machining of Medical Electrodes made from MP35N(R)", Jun. 23, 2020, Metal Cutting Corporation (Year: 2020).
Extended European Search Report dated Mar. 23, 2022, from European Application No. 21204799.7.
Extended European Search Report dated Sep. 23, 2022, from corresponding European Application No. 22168805.4.

* cited by examiner

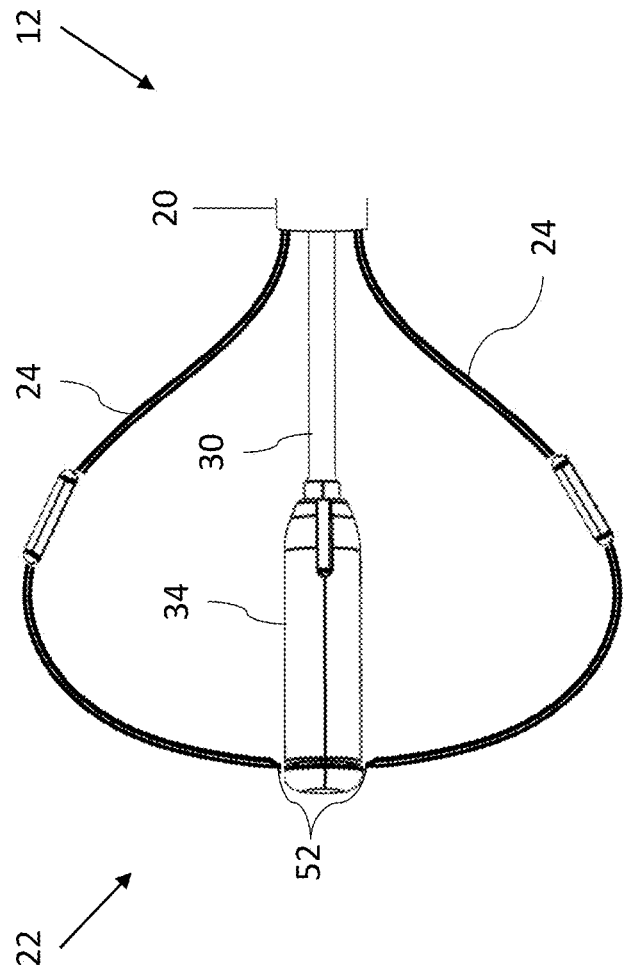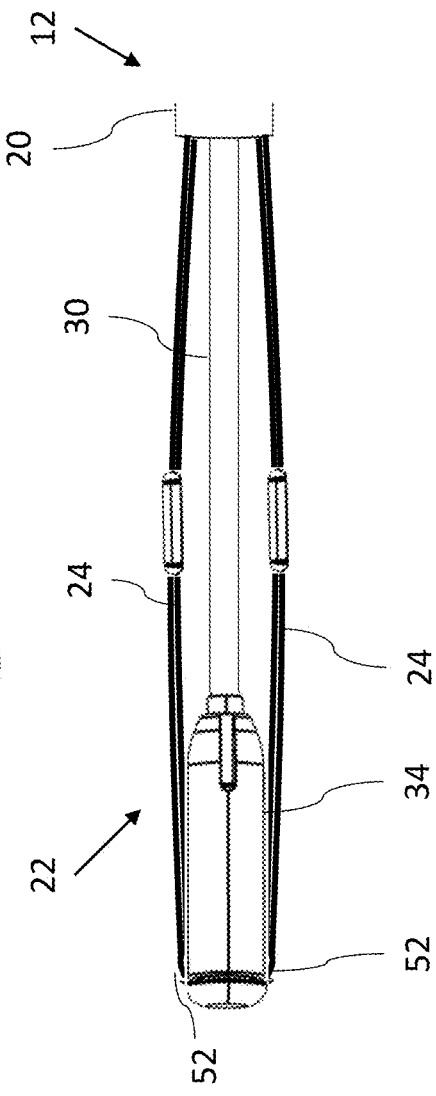
FIG 7A
FIG. 7B

SURFACE MOUNTED ELECTRODE CATHETER

RELATED APPLICATION INFORMATION

The present application claims benefit of U.S. Provisional Patent Application Ser. No. 63/076,614 of Beeckler, et al., filed 10 Sep. 2020, the disclosure of which is hereby incorporated herein by reference.

FIELD OF THE INVENTION

The present invention relates to medical devices, and in particular, but not exclusively to, catheters with electrodes.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied between the tip electrode(s) of the ablating catheter, and the reference electrode, flowing through the media between the electrodes it, i.e., blood and tissue. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

US Patent Publication 2014/0276733 of VanScoy, et al., describes an ablation catheter including an elongated body having a proximal end and a distal end. At least one ablation element is disposed on the body between the proximal end and the distal end and configured to ablate renal tissue to control hypertension. At least one localization sensor is disposed on the body and configured to interact with a magnetic field. The at least one localization sensor aids in determining an appropriate target tissue for ablation.

US Patent Publication 2008/0125772 of Stone, et al., describes a catheter and catheter system using energy tailored for remodeling and/or removal of target material along a body lumen, often of atherosclerotic material of a blood vessel of a patient. An elongate flexible catheter body with a radially expandable structure may have a plurality of electrodes or other electrosurgical energy delivery surfaces to radially engage atherosclerotic material when the structure expands. An atherosclerotic material detector system may measure and/or characterize the atherosclerotic material and its location, optionally using impedance monitoring.

US Patent Publication 2011/0137298 of Nguyen, et al., describes an ablation apparatus comprising an ultrasonic transducer which includes a piezoelectric element having a cylindrical shape; a plurality of external electrodes disposed on the outer surface of the piezoelectric element; and at least one internal electrode disposed on the inner surface of the piezoelectric element. The internal electrode(s) provides corresponding internal electrode portions that are disposed opposite the external electrodes with respect to the piezoelectric element, the external electrodes and the at least one internal electrode to be energized to apply an electric field across the piezoelectric element. The ultrasonic ablation zones of the external electrodes are distributed in a staggered configuration so as to span one or more open arc segments around the longitudinal axis, and the ultrasound ablation zones of all external electrodes projected longitudinally onto any lateral plane which is perpendicular to the longitudinal axis span a substantially closed loop around the longitudinal axis.

US Patent Publication 2012/0067640 of Moulin, et al., describes an electrical connection making it possible to achieve leak-tight electrical linking in an environment that is subjected to corrosive gases or liquids, wherein the connection comprises: at least two conductors for forming said electrical connection between each other or with a connector element; an outer insulating layer formed on each of said conductors and made up of a fluorinated polymer that is meltable at a temperature situated between the temperature of said environment and a predetermined higher temperature; a heat-shrink sleeve surrounding said conductors and made up of an outer layer of heat-shrink polymer and an inner layer of said fluorinated polymer that is meltable at a temperature situated between the temperature of said environment and said predetermined higher temperature; melting said outer insulating layers of said conductors and said inner layer of said heat-shrink sleeve by heating to a temperature higher than said temperature of said environment and lower than said predetermined higher temperature, thereby making a weld that is continuous and leak-tight, and of controlled thickness.

US Patent Publication 2013/0131661 of Jackson, et al., describes a method and apparatus for treating abnormal mucosa in the esophagus, such that the depth of the treated tissue is controlled. The depth of ablation is controlled by monitoring the tissue impedance and/or the tissue temperature. A desired ablation depth is also achieved by controlling the energy density or power density, and the amount of time required for energy delivery. A method and apparatus are disclosed for measuring an inner diameter of a body lumen, where a balloon is inflated inside the body lumen at a fixed pressure.

U.S. Pat. No. 3,359,525 describes an electric heating element heat-stable up to temperatures of about 600 degrees Fahrenheit, which comprises: (a) an electric heat generating unit comprising carbon dispersed in a binder of a material selected from the group consisting of aromatic polyimides, aromatic polyamides and aromatic polybenzimidazoles, said unit having means for connecting it to an electric power source; and (b) an electrically-insulating heat conductive coating in adherent contact with the surface of said unit, said coating comprising a polymer selected from the group consisting of aromatic polyimides, aromatic polyamides and aromatic polybenzimidazoles.

SUMMARY

There is provided in accordance with an embodiment of the present disclosure, a medical system including a catheter configured to be inserted into a body part of a living subject, and including an elongated deflectable element including a distal end, a proximal coupler connected to the distal end, an expandable assembly including a plurality of flexible polymer circuit strips, the flexible polymer circuit strips having respective proximal ends connected to, and disposed circumferentially around, the proximal coupler, respective ones of the flexible polymer circuit strips including respective multiple strip electrodes, respective contact arrays disposed at the respective proximal ends, and respective multiple circuit traces electrically connecting the respective multiple strip electrodes with the respective contact arrays, and a plurality of surface mountable electrodes mounted on, and bulging over respective ones of the flexible polymer circuit strips.

Further in accordance with an embodiment of the present disclosure the catheter further includes first insulated electrical wires disposed in the elongated deflectable element, respective groups of the first insulated electrical wires being electrically connected to the respective contact arrays of respective ones of the flexible polymer circuit strips, and second insulated electrical wires disposed in the elongated deflectable element, respective ones of the second insulated electrical wires being run externally to respective ones of the flexible polymer circuit strips and being electrically connected to respective ones of the surface mountable electrodes.

Still further in accordance with an embodiment of the present disclosure the first insulated electrical wires include electrically insulating material which is configured to have a temperature rating between 150 and 200 degrees Centigrade, and the second insulated electrical wires include electrically insulating material which is configured to have a temperature rating greater than 200 degrees Centigrade.

Additionally, in accordance with an embodiment of the present disclosure respective ones of the first insulated electrical wires have a first wire gauge, respective ones of the second insulated electrical wires have a second wire gauge, and the first wire gauge is greater than the second wire gauge.

Moreover, in accordance with an embodiment of the present disclosure the catheter includes respective shrink-sleeves securing respective ones of the second wires to respective ones of the flexible polymer circuit strips.

Further in accordance with an embodiment of the present disclosure respective ones of the surface mountable electrodes are mounted externally to the respective shrink-sleeves of respective ones of the flexible polymer circuit strips.

Still further in accordance with an embodiment of the present disclosure the catheter includes respective cable jackets disposed in the elongated deflectable element, the respective groups of the first insulated electrical wires are disposed in respective ones of the cable jackets, and respective ones of the second insulated electrical wires are disposed in respective ones of the cable jackets among the respective groups of the first insulated wires.

Additionally, in accordance with an embodiment of the present disclosure each respective one of the surface mountable electrodes extends around the respective flexible polymer circuit strip.

Moreover in accordance with an embodiment of the present disclosure, the system includes an ablation power generator configured to be connected to the catheter, and apply an electrical signal to at least one of the surface mountable electrodes to ablate a tissue of the body part, and a mapping module configured to receive electrical signals from ones of the strip electrodes of the flexible polymer circuit strips, and generate an electro-anatomical map responsively to the received electrical signals.

Further in accordance with an embodiment of the present disclosure the catheter includes a pusher including a distal portion, and being configured to be advanced and retracted through the deflectable element, the catheter includes a distal coupler connected to the distal portion of the pusher, and the flexible polymer circuit strips are disposed circumferentially around the distal portion of the pusher, the flexible polymer circuit strips have respective distal ends connected to the distal coupler, and the strips being configured to bow radially outward when the pusher is retracted expanding the expandable assembly from a collapsed form to an expanded form.

There is also provided in accordance with another embodiment of the present disclosure, a catheter device configured to be inserted into a body part of a living subject, and including an elongated deflectable element including a distal end, a distal end assembly disposed at the distal end and including a plurality of first electrodes and a plurality of second electrodes, first insulated electrical wires disposed in the elongated deflectable element, respective ones of the first insulated electrical wires being electrically connected to respective ones of the first electrodes, the first insulated electrical wires including electrically insulating material which is configured to have a temperature rating between 150 and 200 degrees Centigrade, and second insulated electrical wires disposed in the elongated deflectable element, respective ones of the second insulated electrical wires being electrically connected to respective ones of the second electrodes, the second insulated electrical wires including electrically insulating material which is configured to have a temperature rating greater than 200 degrees Centigrade.

Still further in accordance with an embodiment of the present disclosure, the device includes shrink-sleeves covering at least part of the second insulated electrical wires.

There is also provided in accordance with still another embodiment of the present disclosure, a method of manufacturing a catheter including providing a catheter including an elongated deflectable element, a proximal coupler connected to a distal end of the elongated deflectable element, and an expandable assembly including a plurality of flexible polymer circuit strips, the flexible polymer circuit strips having respective proximal ends connected to, and disposed circumferentially around, the proximal coupler, respective ones of the flexible polymer circuit strips including respective multiple strip electrodes, respective contact arrays disposed at the respective proximal ends, and respective multiple circuit traces electrically connecting the respective multiple strip electrodes with the respective contact arrays, and mounting a plurality of surface mountable electrodes over respective ones of the flexible polymer circuit strips with the surface mountable electrodes bulging over the respective ones of the flexible polymer circuit strips.

Additionally in accordance with an embodiment of the present disclosure, the method includes disposing first insulated electrical wires in the elongated deflectable element, electrically connecting respective groups of the first insulated electrical wires to the respective contact arrays of respective ones of the flexible polymer circuit strips, disposing second insulated electrical wires in the elongated deflectable element, running respective ones of the second insulated electrical wires externally to respective one of the flexible polymer circuit strips, and electrically connecting respective ones of the second insulated electrical wires to respective ones of the surface mountable electrodes.

Moreover, in accordance with an embodiment of the present disclosure the electrically connecting respective groups of the first insulated electrical wires includes melting electrically insulating material of the first wires, and the electrically connecting respective ones of the second insulated electrical wires includes mechanically stripping electrically insulating material of the second insulated electrical wires.

Further in accordance with an embodiment of the present disclosure respective ones of the first insulated electrical wires have a first wire gauge, respective ones of the second insulated electrical wires have a second wire gauge, and the first wire gauge is greater than the second wire gauge.

Still further in accordance with an embodiment of the present disclosure, the method includes shrink-wrapping respective ones of the second insulated electrical wires to respective ones of the flexible polymer circuit strips.

Additionally in accordance with an embodiment of the present disclosure, the method includes disposing respective shrink-sleeves around respective ones of the second insulated electrical wires and respective ones of the flexible polymer circuit strips, pulling respective ones of the second insulated electrical wires through respective holes in respective ones of the shrink-sleeves, heat shrinking respective distal portions of respective ones of the shrink-sleeves, sliding respective ones of the surface mountable electrodes over the respective heat shrunk distal portions of respective ones of the shrink-sleeves, electrically connecting respective ones of the second insulated electrical wires to respective ones of the surface mountable electrodes, removing slack in respective ones of the second insulated electrical wires, and heat shrinking respective proximal portions of respective ones of the shrink-sleeves.

Moreover, in accordance with an embodiment of the present disclosure, the method includes disposing the respective groups of the first insulated electrical wires in respective cable jackets, and disposing respective ones of the second insulated electrical wires in respective ones of the cable jackets among the respective groups of the first insulated wires.

BRIEF DESCRIPTION OF THE DRAWINGS

The present invention will be understood from the following detailed description, taken in conjunction with the drawings in which:

FIGS. 7A-B are schematic views illustrating the catheter of FIG. 1 is a deployed form and a collapsed form, respectively;

DESCRIPTION OF EXAMPLE EMBODIMENTS

Overview

Figure 1:
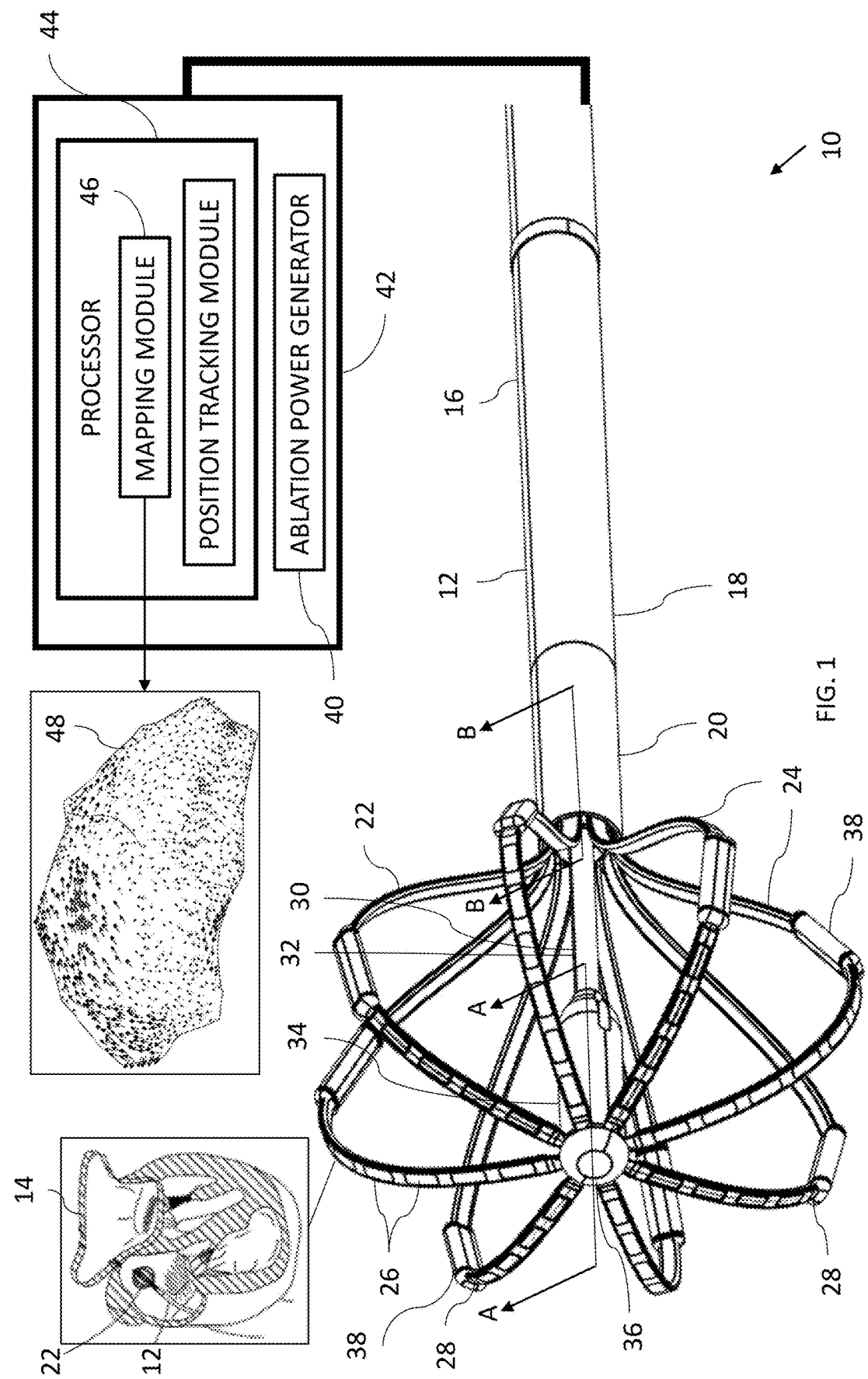
FIG. 1 is a partly pictorial, partly block diagram view of a medical system constructed and operative in accordance with an embodiment of the present invention.

Diagnostic catheters, such as basket catheters, provide many electrodes to capture electrical signals, such as electrical potentials, from tissue of a body part of a patient. The electrical signals may then be analyzed to provide an indication of the medical state of the body part. For example, the electrical signals may be used to provide an electro-anatomical map. The medical state of the body part may indicate that some of the tissue may require ablation (such as radiofrequency (RF) ablation or irreversible electroporation (IRE)) using a suitable catheter. Although the basket catheter electrodes may be suitable for diagnostic purposes, the electrodes and/or the connections to the electrodes may be too small to be used for ablation. This is particularly true for IRE where high currents are used, and a large electrode surface area is needed to provide effective IRE ablation. Therefore, in such situations, the diagnostic basket catheter is removed from the patient, and a suitable ablation catheter is inserted into the body part of the patient, and ablation is performed. Using two catheters increases the length of the medical procedure, may delay essential therapeutic treatment, and may increase trauma of the patient due to the time delay and the use of two catheters.

Embodiments of the present invention solve the above problems by providing a basket catheter which includes both diagnostic electrodes and ablation electrodes thereby providing a combined therapeutic and diagnostic catheter.

The basket catheter includes a distal end expandable assembly made of flexible polymer circuit strips connected together proximally and distally to form a basket. Each strip includes diagnostic electrodes. Each strip also includes an ablation electrode connected to the strip. The ablation electrode of each strip may be slid over that strip, wrapped around that strip, or formed from two parts which are connected together around that strip.

In some embodiments, the ablation electrodes are connected to the flexible polymer circuit strips in a staggered formation with alternate ablation electrodes being disposed more proximally than other ablation electrodes to allow compact stowing of the expandable assembly during insertion of the catheter into the patient and removal of the catheter from the patient.

In some embodiments, each strip includes a contact pad, which is generally formed in the same or similar manner to the diagnostic electrodes. In disclosed embodiments, the contact pad is larger than the diagnostic electrodes. The ablation electrodes are connected to the respective contact pads using a suitable bonding method, such as using solder, conductive epoxy, resistance welding, laser welding, or any other suitable method, to provide an electrical connection between each ablation electrode and the respective contact pad. The ablation electrodes may be connected using one or two bonds. The ablation electrodes are also referred to herein as surface mountable electrodes. The diagnostic electrodes are also referred to herein as strip electrodes. Adhesive may also be used to connect the surface mountable electrodes to the strips in addition to the bonding.

In other embodiments, the ablation electrodes are electrically connected via wires run along the inner surface of the respective flexible polymer circuit strips and through an elongated deflectable element of the catheter to the proximal end of the catheter. Other wires run from the proximal end of the catheter through the deflectable element to respective contact arrays of the flexible polymer circuit strips thereby electrically connecting the diagnostic electrodes to the proximal end of the catheter.

In some embodiments, the wires from the ablation electrodes and the diagnostic electrodes are bundled in cables (e.g., in cable jackets) in the elongated deflectable element. In some embodiments, respective groups of the wires from the diagnostic electrodes are bundled with respective ones of the wires from the ablation electrodes thereby providing better insulation for the ablation electrode wires.

One problem encountered when manufacturing catheters is due to the miniaturization of the elements. For example, a basket catheter may include tens or even more than a hundred electrodes, each requiring a separate electrical connection from the basket to the proximal end of the catheter. Connecting the wires running from the proximal end of the catheter to the contact arrays (e.g., solder pads) of the flexible polymer circuit strips or other elements containing the electrodes is challenging. One solution is to use insulated wires with a low temperature rating (e.g., greater than 150 degrees Centigrade but less than 200 degrees Centigrade) so that the wire insulation melts or degrades when solder is applied to the wire ends (e.g., at about 300 degrees Centigrade) thereby allowing the wires to be connected to the contact arrays without having to strip the insulation from the wires. However, using low temperature rated wire may be problematic when dealing with high temperature situations during manufacture or use of the catheter. For example, heating thermal shrink-sleeves may melt or degrade (e.g., char and cause crumbling) the wire insulation and may lead to electrical shorts between the wires and conducting elements such as metal supports of the flexible polymer circuit strips.

Therefore, embodiments of the present invention solve the above problems by providing a catheter (e.g., a basket catheter or any other suitable catheter, such as, a balloon catheter, or a Lasso catheter) which uses insulated wires with a low temperature-rating (e.g., between 150 and 200 degrees Centigrade) to electrically connect electrodes where the wire insulation is not subject to melting or heat degradation other than when soldered to connections or where wire insulation is not important (e.g., the lack of insulation does not lead to shorts), and uses insulated wires with a higher temperature rating (e.g., more than 200 degrees Centigrade) to electrically connect electrodes where heat is applied the wires during manufacture and/or use of the catheter and could lead to shorts or other problems.

The term "temperature rating", as used in the specification and claims, is defined as the maximum continuous temperature that the wire insulation can withstand during its lifetime without causing thermal damage, such as melting or thermal degradation (e.g., charring and crumbling) of the wire insulation.

In some embodiments, the catheter uses wires with a low temperature rating (e.g., between 150 and 200 degrees Centigrade) (running from the proximal end of the catheter) which are electrically connected to the contact arrays (which in turn are electrically connected to diagnostic electrodes on the circuit strips via circuit traces) thereby allowing the wires to be connected using soldering without stripping the insulation from the wires. Other wires running from the proximal end of the catheter have a higher temperature rating (e.g., more than 200 degrees Centigrade) which are stripped prior to being electrically connected to the ablation electrodes mounted on the circuit strips. The wires with the higher temperature rating may be connected to the respective circuit strips using thermal shrink-sleeves without be concerned that the application of heat to the shrink-sleeves will melt or degrade the insulation of the higher temperature rated wires.

In some embodiments, a mapping module run by a processor receives electrical signals from at least some of the strip electrodes of the flexible polymer circuit strips and generates an electro-anatomical map responsively to the received electrical signals. An ablation power generator is connected to the catheter and applies an electrical signal to one or more of the surface mountable electrodes to ablate (using RF or IRE ablation) the tissue of the body part. In some embodiments, the ablation power generator applies an electrical signal between at least some of the surface mountable electrodes.

In some embodiments, the catheter may include an electrode, referred to herein as a distal electrode, placed at the distal tip of the catheter between the distal ends of the strips. The distal electrode may be used for ablation. In some embodiments, the ablation power generator applies an electrical signal between one or more of the surface mountable electrodes and the distal electrode to ablate (using RF or IRE ablation) the tissue of the body part.

System Description

Reference is now made to FIG. 1, which is a partly pictorial, partly block diagram view of a medical system 10 constructed and operative in accordance with an embodiment of the present invention. The medical system 10 includes a catheter 12 configured to be inserted into a body part 14 (e.g., heart chamber) of a living subject.

The catheter 12 includes an elongated deflectable element 16 including a distal end 18. The elongated deflectable element 16 may have any suitable outer diameter and length, for example, the outer diameter may be in a range between 1 mm and 4 mm and the length may be in a range between 1 cm and 15 cm.

The catheter 12 also includes a proximal coupler 20 connected to the distal end 18. The proximal coupler 20 may be formed as an integral part of the deflectable element 16 or as a separate element, which is then connected to the distal end 18 using any suitable connection method, such as using adhesive, for example, epoxy. The catheter 12 also includes an expandable distal end assembly 22 including flexible polymer circuit strips 24 (only some labeled for the sake of simplicity). Each flexible polymer circuit strip 24 includes multiple strip electrodes 26 (only some labeled for the sake of simplicity) and a respective contact pad 28 disposed thereon. The contact pads 28 are mostly obscured in FIG. 1 and are shown more clearly in FIGS. 8-10, 13, and 14. The catheter 12 includes a pusher 30 including a distal portion 32. The pusher 30 is configured to be advanced and retracted through the deflectable element 16. The catheter 12 also includes a distal coupler 34 connected to the distal portion 32 of the pusher 30. Proximal ends of the flexible polymer circuit strips 24 are connected to the proximal coupler 20, and distal ends of the flexible polymer circuit strips 24 are connected to the distal coupler 34 with the flexible polymer circuit strips 24 being disposed circumferentially around the distal portion 32 of the pusher 30. The flexible polymer circuit strips 24 are configured to bow radially outward when the pusher 30 is retracted expanding the expandable assembly from a collapsed form to an expanded form, described in more detail with reference to FIGS. 7A-B.

In some embodiments, the catheter 12 includes a distal electrode 36 disposed at a distal tip of the catheter 12 between the distal ends of the flexible polymer circuit strips 24. In other embodiments, the catheter 12 includes a nose cap (not shown) disposed in the distal coupler 34 instead of the distal electrode 36.

The catheter 12 includes surface mountable electrodes 38 electrically connected to respective one of the flexible polymer circuit strips 24. In some embodiments, one surface mountable electrode 38 is disposed on each flexible polymer circuit strip 24. The surface mountable electrodes 38 are electrically connected to the flexible polymer circuit strips 24 via the contact pads 28, as described in more detail with reference to FIG. 13.

The surface mountable electrodes 38 may be connected at the same position on each flexible polymer circuit strip 24 or in a staggered formation with alternate surface mountable electrodes 38 being disposed more proximally than other surface mountable electrodes 38 so that the expandable assembly 22 may compact efficiently when stowed during insertion into, and removal from the body part 14 of the patient.

In some embodiments, the surface mountable electrodes 38 may be connected to any suitable basket catheter with elements that differ from the elements of the catheter 12.

The medical system 10 includes an ablation power generator 40 configured to be connected to the catheter 12. The ablation power generator 40 may be housed in a console 42. The ablation power generator 40 is configured to apply an electrical signal to one or more of the surface mountable electrodes 38 to ablate tissue of the body part 14. In some embodiments, the ablation power generator 40 is configured to apply an electrical signal between some of the surface mountable electrodes 38 to ablate (using RF or IRE ablation) the tissue. In some embodiments, the ablation power generator 40 is configured to apply an electrical signal between one or more of the surface mountable electrodes 38 and the distal electrode 36 to ablate (using RF or IRE ablation) the tissue of the body part 14.

The medical system 10 includes a processor 44, which is configured to execute a mapping module 46 configured to: receive electrical signals from at least some of the strip electrodes 26 of the flexible polymer circuit strips 24; and generate an electro-anatomical map 48 responsively to the received electrical signals.

In practice, some or all of the functions of the processor 44 may be combined in a single physical component or, alternatively, implemented using multiple physical components. These physical components may comprise hard-wired or programmable devices, or a combination of the two. In some embodiments, at least some of the functions of the processor 44 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The medical system 10 may include other modules and elements which are not shown for the sake of simplicity, such as an electrocardiogram module, a display screen, and user input devices (e.g., keyboard and mouse), by way of example only.

Figure 2:
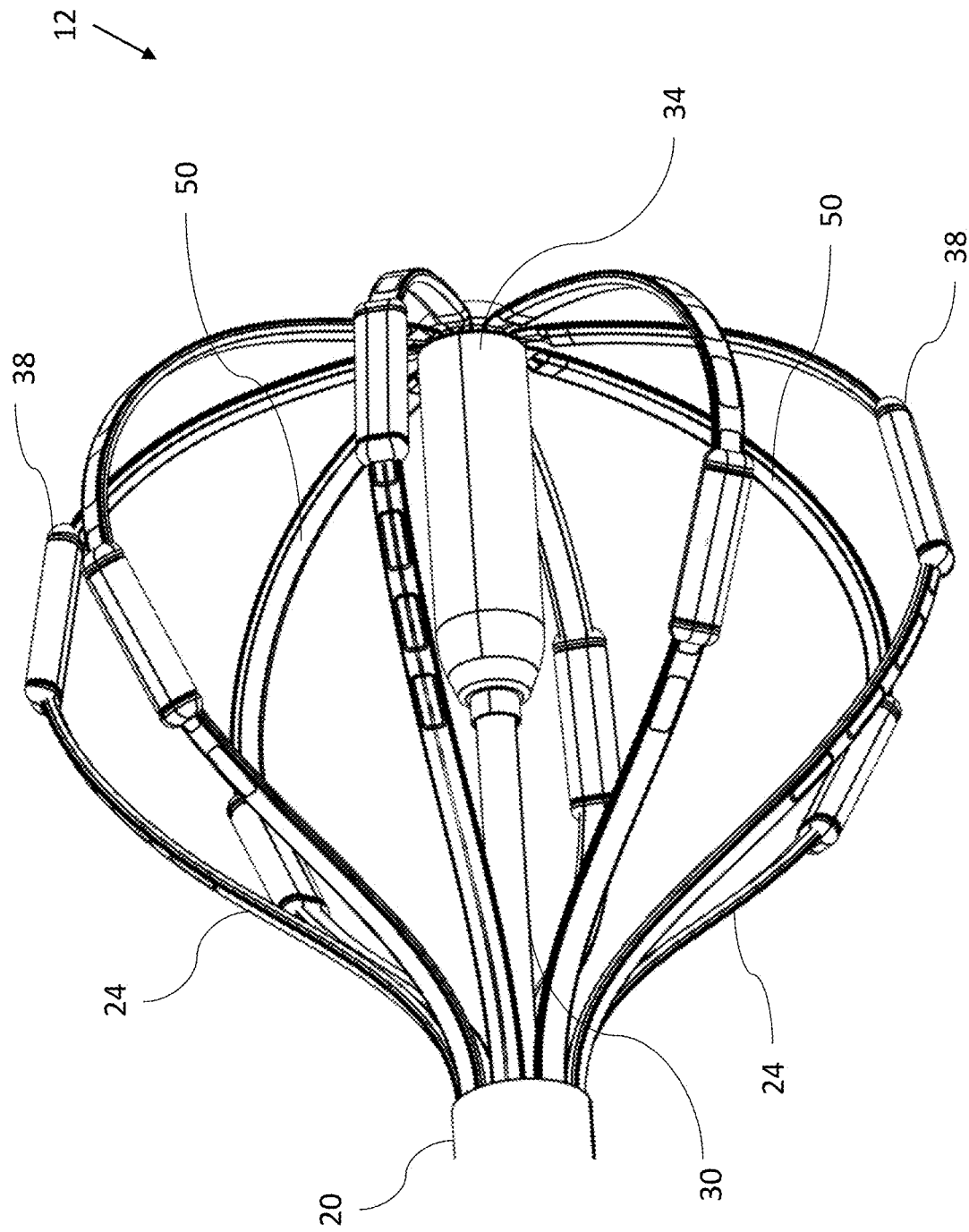
FIG. 2 is a schematic view of a catheter of the system of FIG. 1.

Reference is now made to FIG. 2, which is a schematic view of the catheter 12 of the system 10 of FIG. 1. FIG. 2 shows the proximal coupler 20, the distal coupler 34, the flexible polymer circuit strips 24 (only some labeled for the sake of simplicity), the pusher 30, and the surface mountable electrodes 38 (only some labeled for the sake of simplicity) in more detail.

The inner diameter of the pusher 30 is sized to accommodate wiring. The pusher 30 may be formed from any suitable material, for example, but not limited to polyimide with or without braiding, polyether ether ketone (PEEK) with or without braiding, or polyamide with or without braiding. The distal coupler 34 and the proximal coupler 20 may be formed from any suitable material, for example, but not limited to polycarbonate with or without glass filler, PEEK with or without glass filler, or PEI with or without glass filler.

The catheter 12 includes elongated resilient support elements 50 (only some labeled for the sake of simplicity) connected along a given length of respective ones of the flexible polymer circuit strips 24 providing a shape of the expandable assembly 22 in the expanded form of the expandable assembly 22. The elongated resilient support elements 50 may include any suitable material, for example, but not limited to, Nitinol and/or Polyetherimide (PEI). The elongated resilient support elements 50 extend along the inner surface of the respective strips 24 from the proximal coupler 20 until just before the flexible polymer circuit strips 24 enter the distal coupler 34 to allow the flexible polymer circuit strips 24 to bend sufficiently at that point, as described in more detail with reference to FIGS. 4A-C. The elongated resilient support elements 50 may have any suitable thickness, for example, in the range of about 0.025 mm to 0.25 mm.

Figure 3:
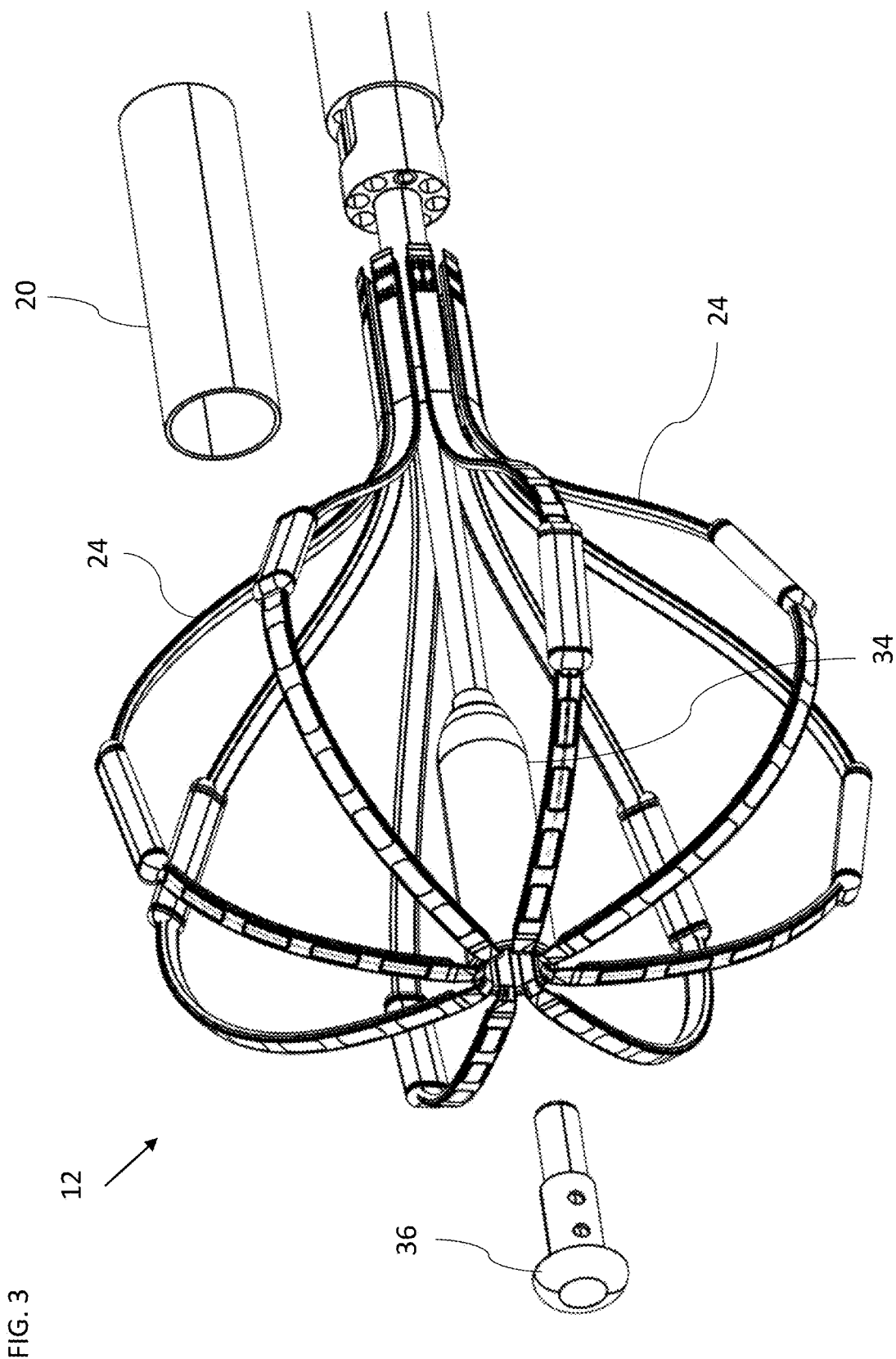
FIG. 3 is a partially exploded view of the catheter of FIG. 2.

Reference is now made to FIG. 3, which is a partially exploded view of the catheter 12 of FIG. 2. FIG. 3 shows the catheter 12 with the distal electrode 36 (or nose piece) and the proximal coupler 20 removed to illustrate how the flexible polymer circuit strips 24 are connected to the distal coupler 34 and the proximal coupler 20. The proximal ends of the flexible polymer circuit strips 24 are connected to, and disposed circumferentially around, an inner surface of the proximal coupler 20. The distal ends of the flexible polymer circuit strips 24 are connected to, and disposed circumferentially around, an inner surface of the distal coupler 34. The flexible polymer circuit strips 24 may be connected to the proximal coupler 20 and distal coupler 34 using any suitable method, for example, using adhesive (e.g., epoxy) and/or using a pressure fit. The distal ends of the flexible polymer circuit strips 24 are generally bent over and connected to the distal end of the distal coupler 34 to allow the flexible polymer circuit strips 24 to bend at almost 90 degrees to form a flat nose catheter. In some embodiments, the distal ends of the flexible polymer circuit strips 24 may be connected to an outer surface of the distal coupler 34 or together without using a distal coupler.

Figure 4B:
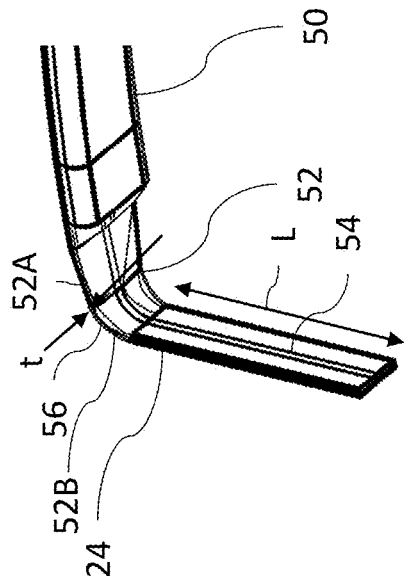
FIGS. 4B-C are schematic views of a distal end of a flexible polymer circuit strip of the catheter of FIG. 2.
Figure 4C:
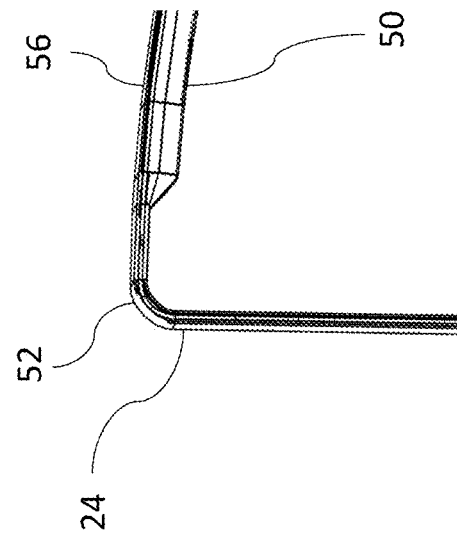
Figure 4A:
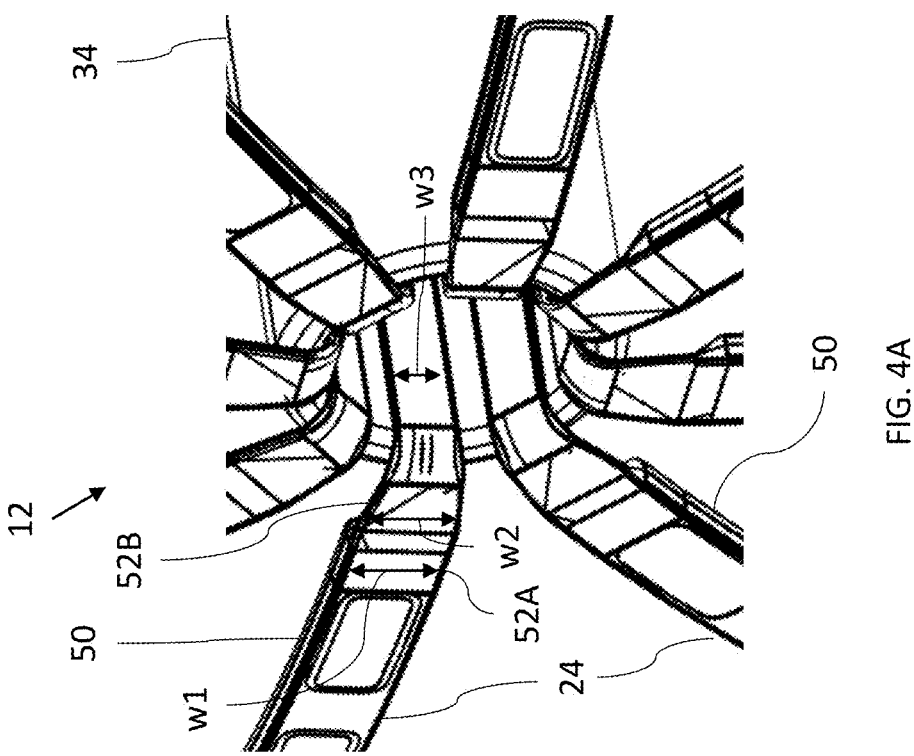
FIG. 4A is schematic view of a distal end of the catheter of FIG. 2 without a distal electrode.

Reference is now made to FIG. 4A, which is schematic view of a distal end of the catheter 12 of FIG. 2 without the distal electrode 36. Reference is also made to FIGS. 4B-C, which are schematic views of a distal end of one of the flexible polymer circuit strips 24 of the catheter 12 of FIG. 2. FIG. 4A shows that the distal ends of the flexible polymer circuit strips 24 bend into the distal coupler 34. In some embodiments, the distal ends of the flexible polymer circuit strips 24 are tapered in order for the flexible polymer circuit strips 24 to fit into the distal coupler 34.

As previously mentioned, the flexible polymer circuit strips 24 are supported using the elongated resilient support elements 50 which extend from the proximal ends of the flexible polymer circuit strips 24 until a hinge section 52 of each flexible polymer circuit strip 24. The hinge section 52 may be reinforced using any suitable material. In some embodiments, the hinge section 52 is reinforced using a yarn 54 (FIG. 4B) that runs from between the flexible polymer circuit strip 24 and the elongated resilient support element 50 until the distal end of the flexible polymer circuit strip 24. The yarn 54 may comprises any one or more of the following: an ultra-high-molecular-weight polyethylene yarn; or a yarn spun from a liquid-crystal polymer. The yarn 54 may be any suitable linear density, for example, in a range between approximately 25 denier and 250 deniers. The flexible polymer circuit strip 24, elongated resilient support element 50, and yarn 54 may be connected together using any suitable method, for example, using an adhesive such as epoxy, and may be covered with a suitable covering 56 (FIGS. 4B and 4C), e.g., thermoplastic polyethylene terephthalate (PET) shrink-sleeves. Windows are opened in the covering 56 to reveal the strip electrodes 26 and the contact pads 28 (FIG. 1).

It can also be seen in FIG. 4B that the hinge section 52 is much thinner, having a thickness "t", than the region including the elongated resilient support element 50. The hinge section 52 may have any suitable thickness, for example, in the range of about 10 to 140 microns. The hinge section 52 is provided with a first portion 52A having a width w1 (FIG. 4A) that tapers to a narrower width w2 in a second portion 52B. The hinge section 52, further narrows from width w2 (of 52B) to a width w3 in an end portion 52C. The width 52A is about 2 times width 52C. The length L of the final portion 52C is about 3 mm to ensure that the flexible polymer circuit strips 24 can be retained in coupler 34 without detaching.

Figure 5:
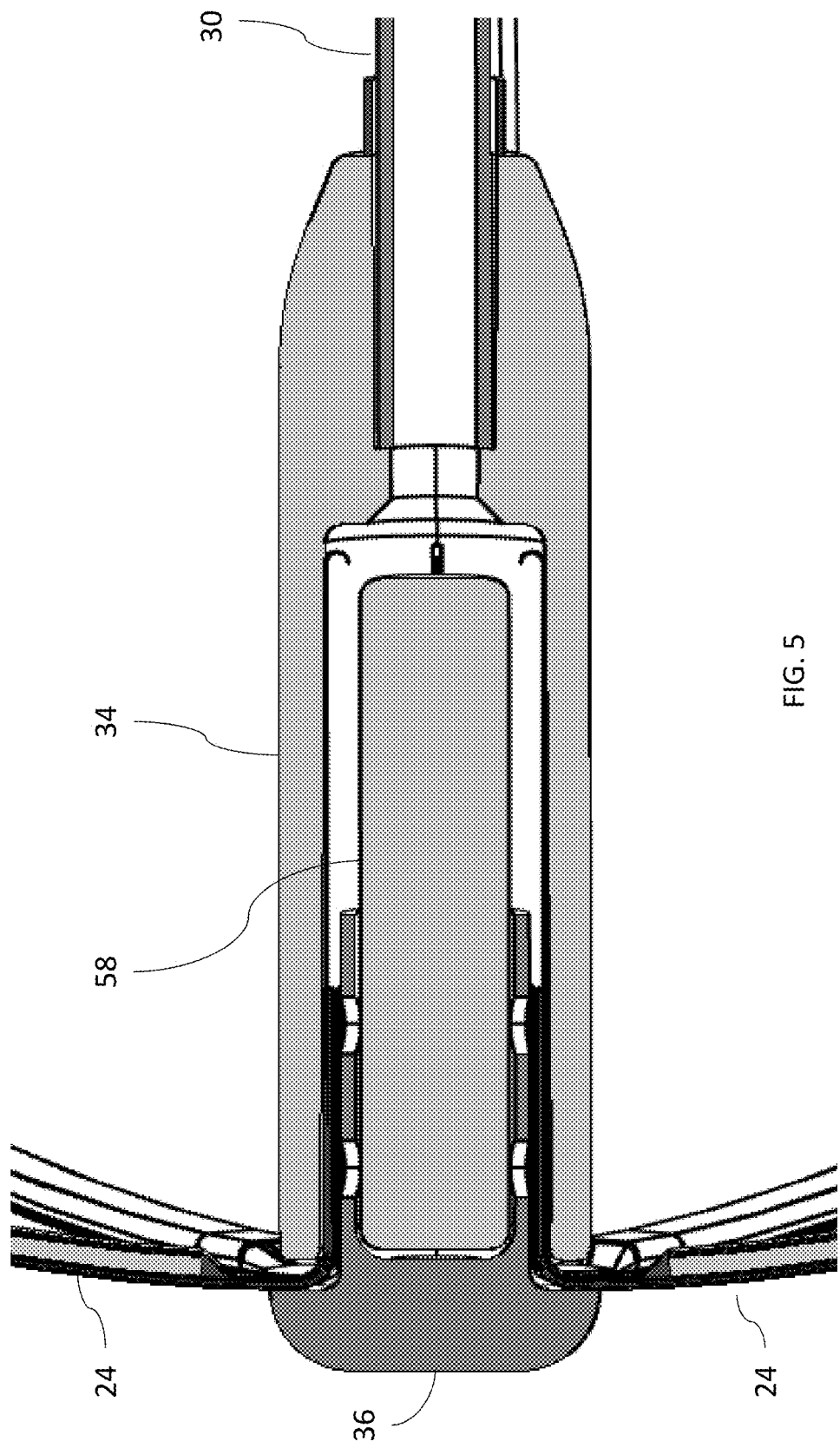
FIG. 5 is a cross-sectional view through line A:A of FIG. 1.

Reference is now made to FIG. 5, which is a cross-sectional view through line A:A of FIG. 1. FIG. 5 illustrates how the distal ends of the flexible polymer circuit strips 24 are connected to the inner surface of the distal coupler 34. A position sensor 58 (such as a magnetic position sensor) is optionally disposed in the distal coupler 34. The distal electrode 36 is inserted into the distal coupler 34 between the flexible polymer circuit strips 24 and the position sensor 58. FIG. 5 illustrates how the distal end of the pusher 30 is connected to the proximal end of the distal coupler 34.

Figure 6:
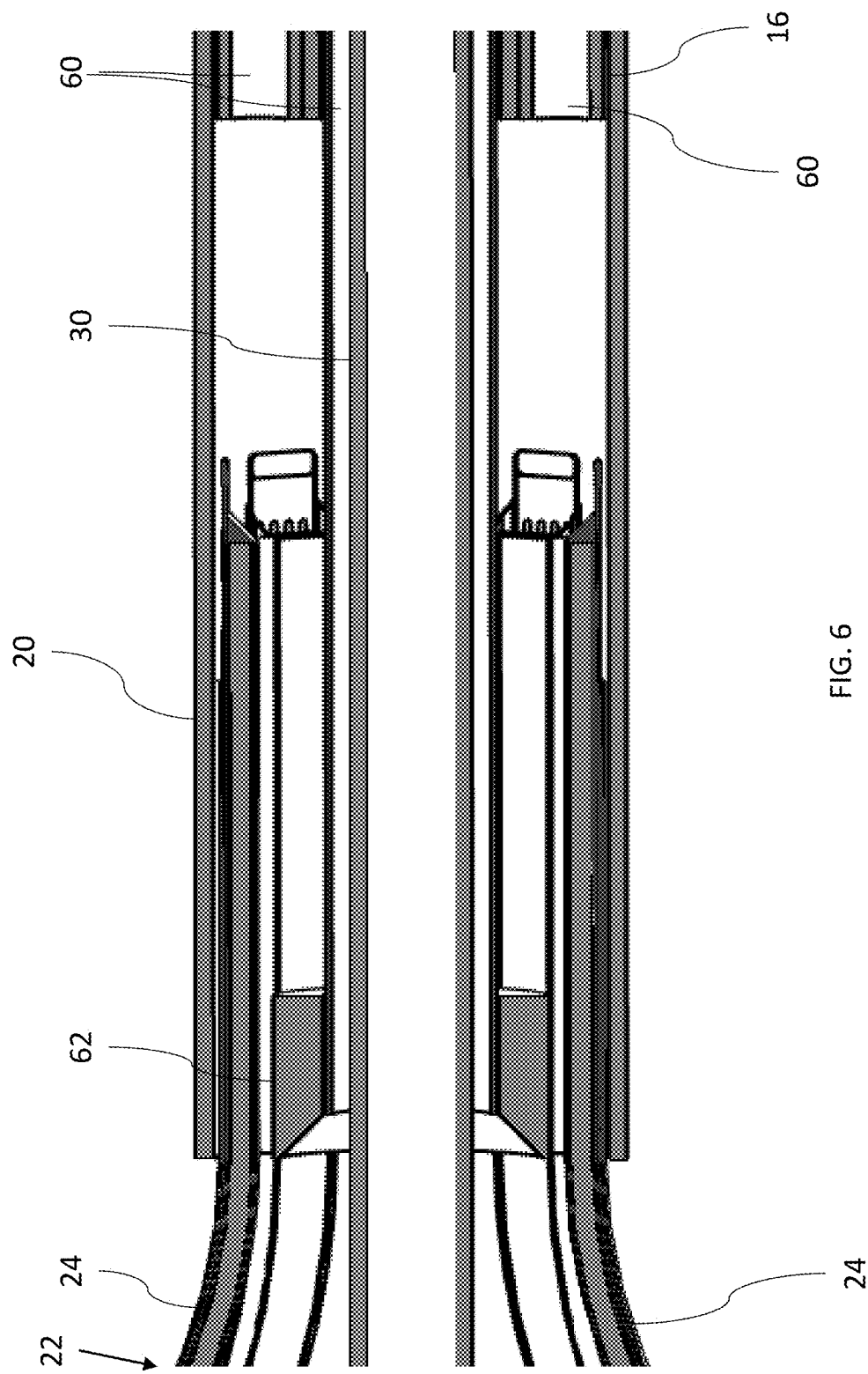
FIG. 6 is a cross-sectional view through line B:B of FIG. 1.

Reference is now made to FIG. 6, which is a cross-sectional view through line B:B of FIG. 1. FIG. 6 illustrates how the proximal ends of the flexible polymer circuit strips 24 are connected to the inner surface of the proximal coupler 20. FIG. 6 also shows that the proximal coupler 20 is connected around an outer surface of the deflectable element 16, which includes lumens 60 to carry wires, and irrigation tubes, for example, from the distal end to the proximal end of the catheter 12. The flexible polymer circuit strips 24 may be additionally held in place using a retaining ring 62. FIG. 6 also shows the pusher 30 extending from one of the lumens 60 of the deflectable element 16 into the expandable assembly 22.

Reference is now made to FIGS. 7A-B, which are schematic views illustrating the catheter 12 of FIG. 1 is a deployed form and a collapsed form, respectively. The flexible polymer circuit strips 24 are configured to bow radially outward when the pusher 30 is retracted expanding the expandable assembly 22 from a collapsed form to an expanded form. The collapsed form of the expandable assembly 22 represents the non-stressed form of the flexible polymer circuit strips 24 which are provided with their shape using the elongated resilient support elements 50 (FIGS. 4A-C). In some embodiments, the non-stressed form of the expandable assembly 22 is the expanded form. In some embodiments, the expandable assembly 22 collapses when retracted into a sheath (not shown) without needing a pusher or similar element.

In some embodiments, the flexible polymer circuit strips 24 are formed as flat strips. The distal ends of the flexible polymer circuit strips 24 are connected to the inner surface of the distal coupler 34 and then the proximal ends of the flexible polymer circuit strips 24 are connected to the proximal coupler 20 so that in the collapsed form, the angle between a tangent to the distal ends of the flexible polymer circuit strips 24 and an axis of the pusher 30 is close to 180 degrees, while in the expanded form, the angle between the tangent to the distal ends of the flexible polymer circuit strips 24 and the axis is about 90 degrees. Therefore, in operation (when the flexible polymer circuit strips 24 are connected to the distal electrode 36 and the proximal coupler 20) the hinge sections 52 are configured to provide a maximum angular range of movement of the flexible polymer circuit strips 24 of about 90 degrees and generally in excess of 80 degrees. However, the hinge section 52 is capable of bending 180 degrees or more.

Figure 8:
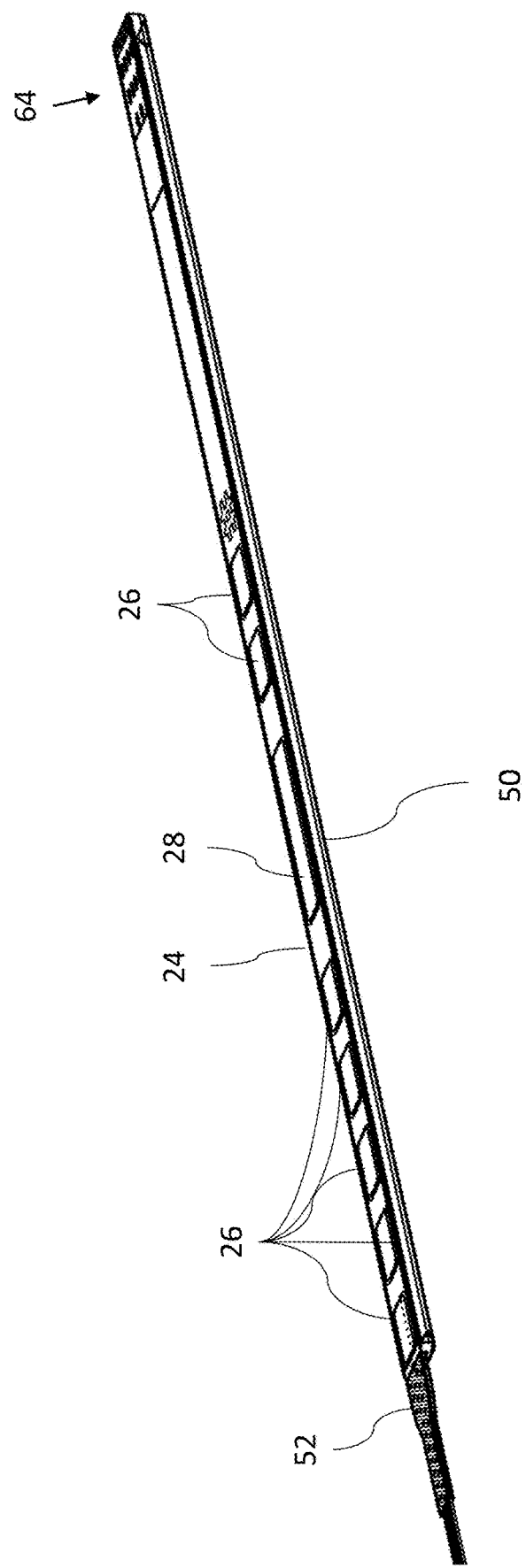
FIG. 8 is a schematic view of a flexible polymer circuit strip of the catheter of FIG. 2.

Reference is now made to FIG. 8, which is a schematic view of one of the flexible polymer circuit strips 24 of the catheter 12 of FIG. 2. The flexible polymer circuit strip 24 shows the strip electrodes 26 and the contact pad 28. The contact pad 28 is typically formed in the same manner as the strip electrodes 26, except that the contact pad 28 may be longer than each strip electrode 26. In some embodiments, the contact pad 28 may be the same size as the strip electrodes 26. FIG. 8 also shows the hinge section 52 and the elongated resilient support element 50 on the lower side of the flexible polymer circuit strip 24. The flexible polymer circuit strip 24 also includes a contact array 64 for connecting the strip electrodes 26, and the contact pad 28 to wires which extend down the deflectable element 16 (FIG. 1) to the proximal end of the catheter 12.

Figure 9:
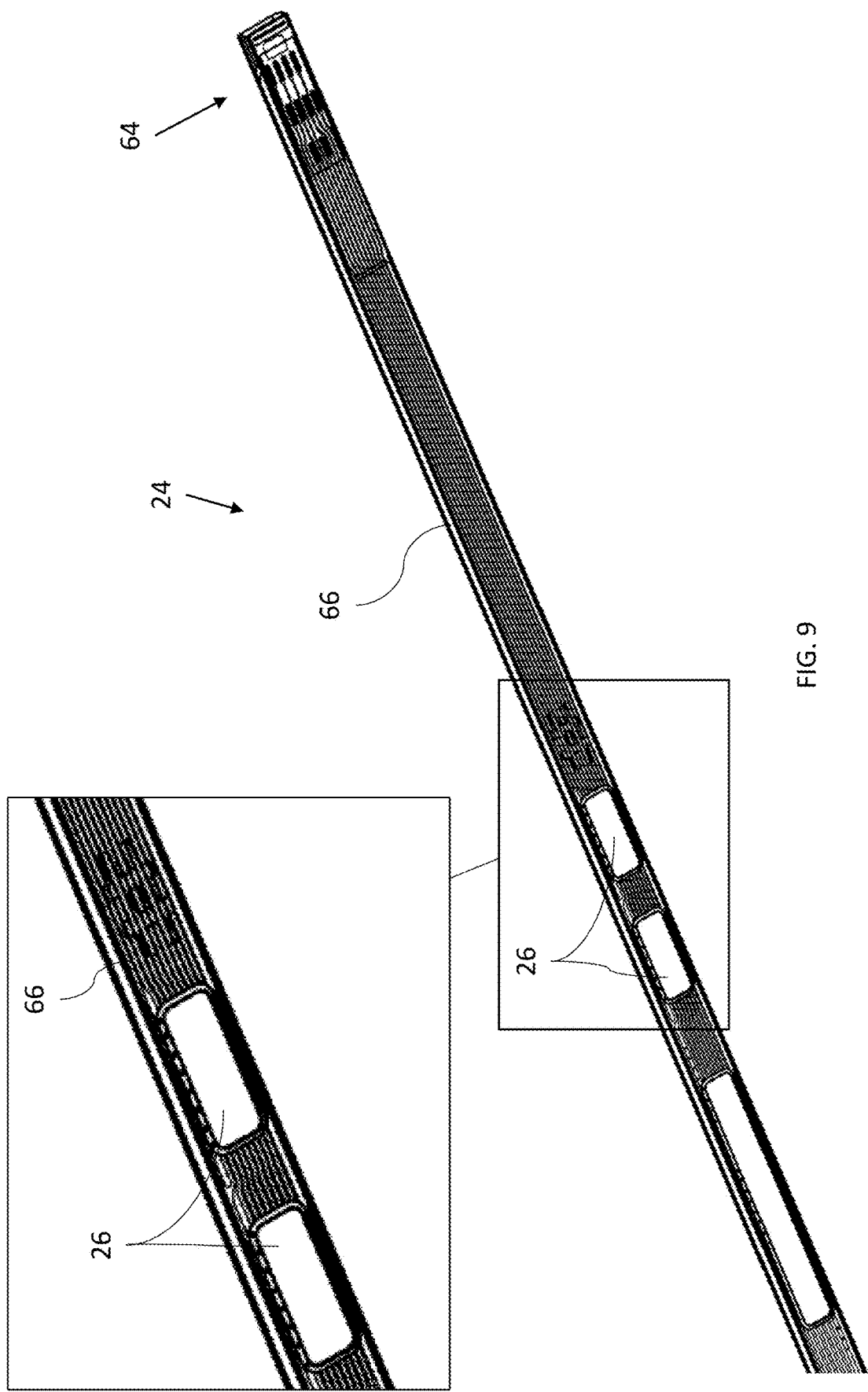
FIGS. 9 and 10 are schematic view of a flexible polymer circuit strip of the catheter of FIG. 2 showing circuit traces.
Figure 10:
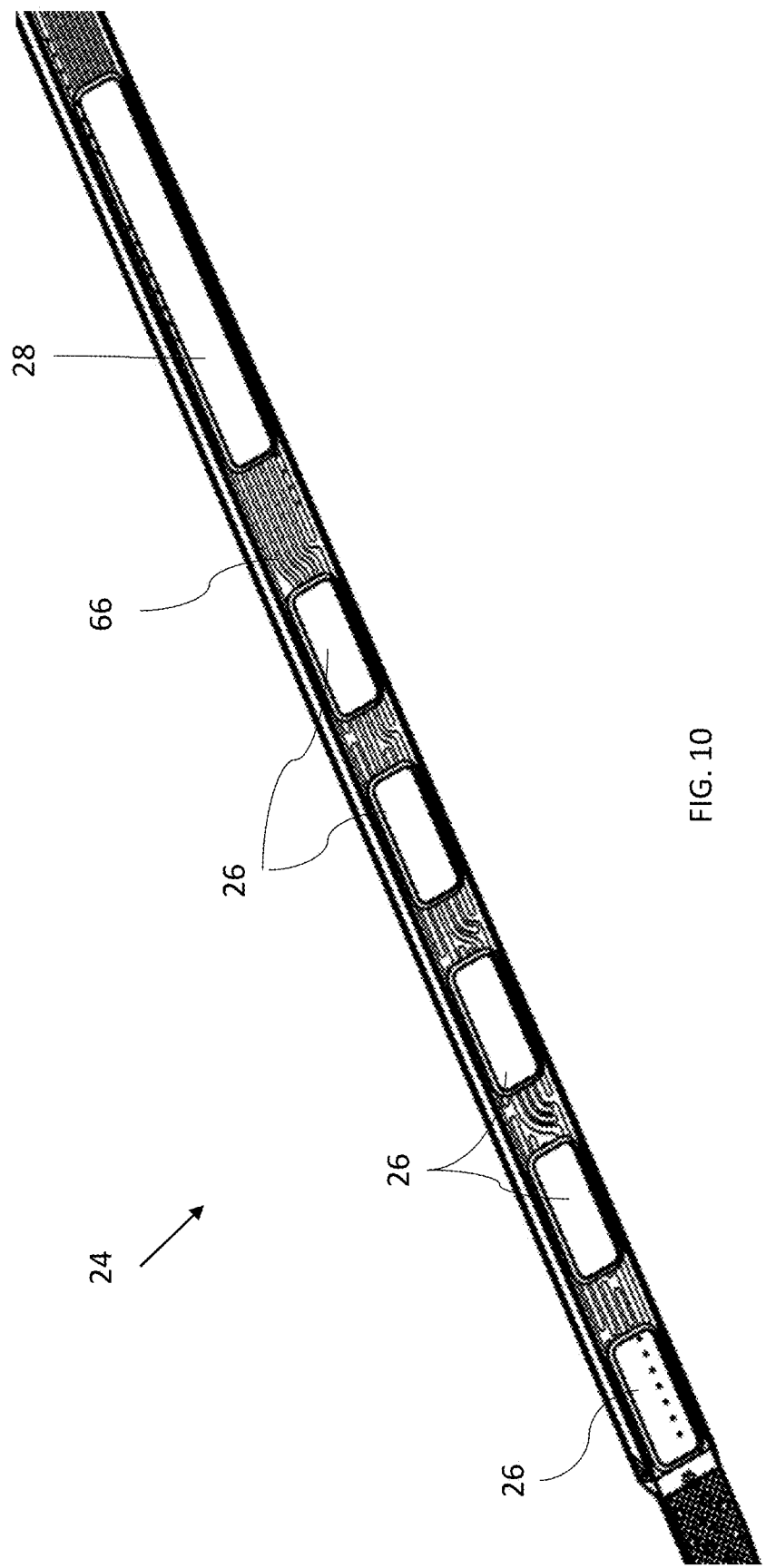

Reference is now made to FIGS. 9 and 10, which are schematic view of one of the flexible polymer circuit strips 24 of the catheter 12 of FIG. 2 showing circuit traces 66. The flexible polymer circuit strip 24 of FIGS. 9 and 10 are shown in a semi-transparent format to allow visualization of different layers of the flexible polymer circuit strip 24. The flexible polymer circuit strip 24 is generally formed from multiple layers including a lower and upper layer. A lower layer of the flexible polymer circuit strip 24 includes the circuit traces 66 which connect the strip electrodes 26 and the contact pad 28 to the contact array 64. The upper layer includes the strip electrodes 26 and the contact pad 28. The circuit traces 66 in the lower layer are connected to the strip electrodes 26 and the contact pad 28 in the upper layer using vias (not shown). The circuit trace 66 to the contact pad 28 may be wider than the other circuit traces 66 and may be spaced further apart from the other circuit traces 66 to ensure proper isolation. The circuit traces 66 for the strip electrodes 26 may be within the range of about 0.005 mm to 0.1 mm wide (e.g., 0.025 mm) with a spacing in the range of about 0.005 mm to 0.1 mm (e.g., 0.025 mm), while the trace 66 for the contact pad 28 may be in the range of about 0.025 mm to 0.25 mm wide (e.g., 0.125 mm wide) with a spacing to the nearest trace in the range of about 0.010 mm to 0.125 mm (e.g., 0.050 mm). The thickness of the traces 66 may be in the range of about 0.005 mm to 0.100 mm (e.g., 0.010 mm). In some embodiments, the circuit traces 66 may have the same width and spacing. The flexible polymer circuit strips 24 may be composed of any suitable materials. In some embodiments, each of the flexible polymer circuit strips 24 comprises a strip of polyimide. The circuit traces 66 are disposed on the back surface of the strip of polyimide and the strip electrodes 26 and contact pad 28 are disposed on the front surface of the strip of polyimide.

The flexible polymer circuit strips 24 may have any suitable dimensions. For example, the length of the flexible polymer circuit strips 24 may be in the range of 10 mm to 60 mm, e.g., 30 mm, the width of the flexible polymer circuit strips 24 may be in the range of about 0.25 mm to 3 mm, e.g., 0.72 mm, and the thickness of the flexible polymer circuit strips 24 may be in the range of about 0.005 mm to 0.14 mm.

Figure 11:
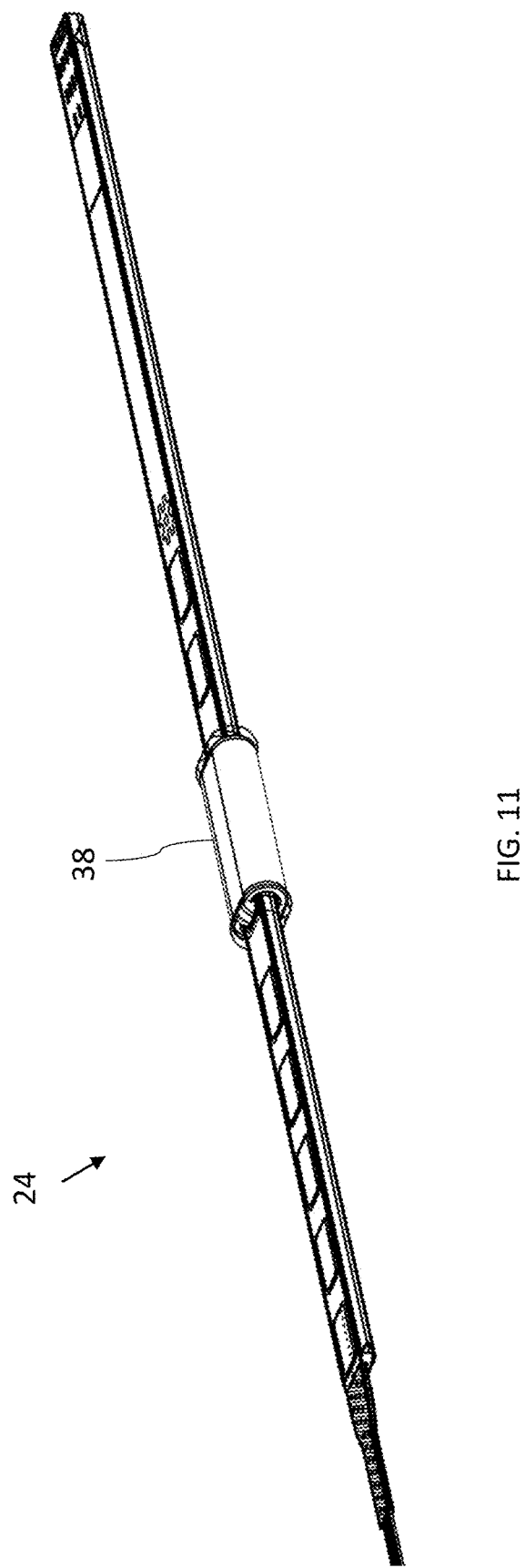
FIG. 11 is a schematic view of the flexible polymer circuit strip of FIG. 8 with a surface mountable electrode mounted thereon.

Reference is now made to FIG. 11, which is a schematic view of the flexible polymer circuit strip 24 of FIG. 8 having mapping electrodes 26 with one of the surface mountable electrodes 38 mounted thereon. The electrodes 26 are used to record electrocardiogram signals generated by the cardiac tissue. Each of the electrode 26 has a first exposed surface area A1. The surface mount electrode 38 can be used for ablation by delivering DC or AC signals via electrode 38. Electrode 38 has a second exposed surface area A2 of at least three times the first exposed area of each mapping electrode 26. The exposed surface area A1 is from about 0.08 mm-squared to about 1 mm-squared. The surface mountable electrode 38 may be formed as a single element which is slid over the flexible polymer circuit strip 24 and the elongated resilient support element 50. In some embodiments, the surface mountable electrode 38 may be formed from two halves which are connected together around strip 24 and the elongated resilient support element 50. In yet other embodiments, the surface mountable electrode 38 may be formed as a band, which is wrapped around the flexible polymer circuit strip 24 and the elongated resilient support element 50. The surface mountable electrodes 38 may be formed from any suitable material, for example, but not limited to gold, gold alloys, platinum, platinum alloys, palladium, or palladium alloys.

Figure 12:
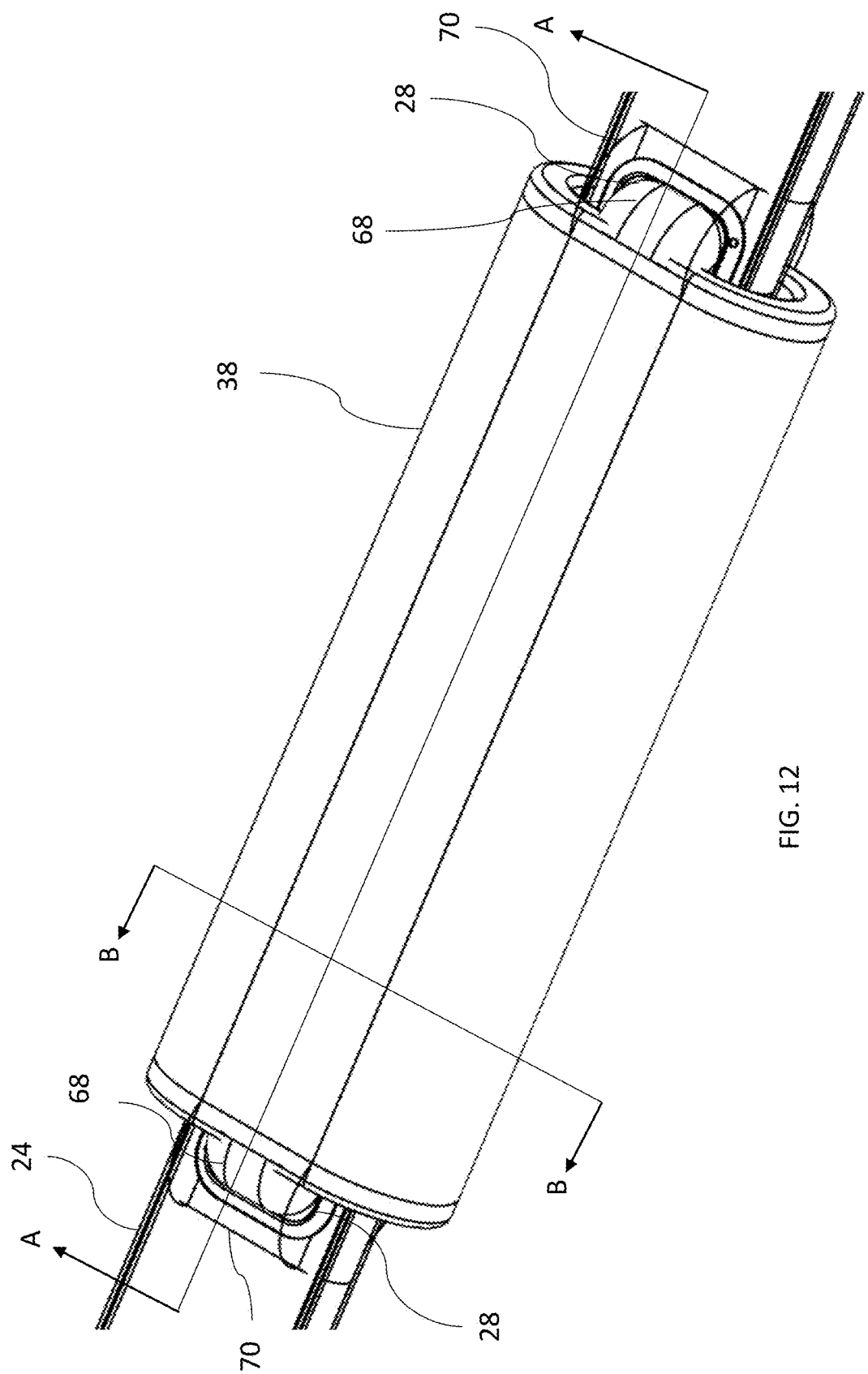
FIG. 12 is a more detailed view of the surface mountable electrode of FIG. 11.

Reference is now made to FIG. 12, which is a more detailed view of the surface mountable electrode 38 of FIG. 11. The surface mountable electrode 38 is shown mounted over the contact pad 28. The surface mountable electrode 38 is electrically connected to the contact pad 28 using two electrically conductive retainers 68 (e.g., using solder, conductive epoxy, resistance welding, laser welding, or any other suitable method). The surface mountable electrode 38 is further secured to the flexible polymer circuit strip 24 using an adhesive 70, such as a polyurethane adhesive or epoxy. The adhesive 70 may be applied so that the contact pad 28 is electrically isolated from the environment around the catheter 12.

Figure 13:
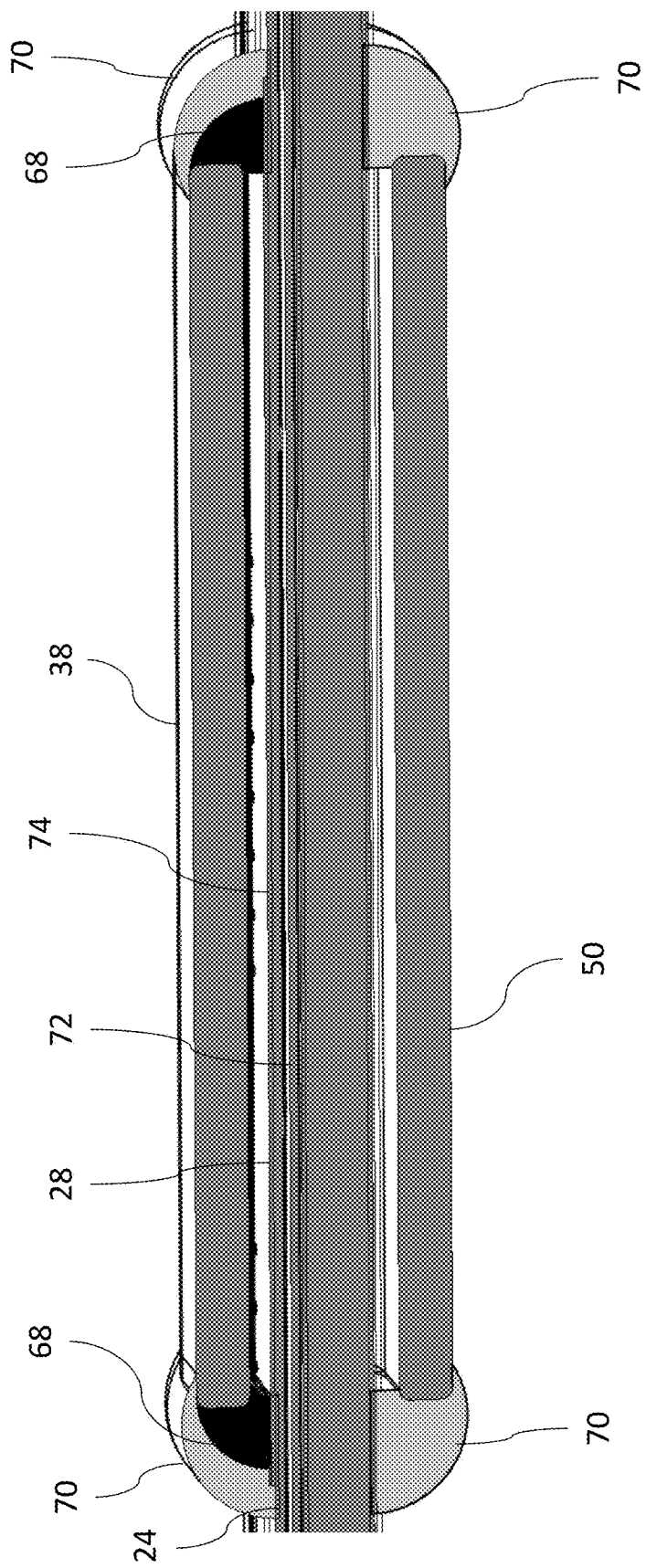
FIG. 13 is a cross-sectional view through line A:A of FIG. 12.

Reference is now made to FIG. 13, which is a cross-sectional view through line A:A of FIG. 12. FIG. 13 shows that the surface mountable electrode 38 extends over the contact pad 28 and below the elongated resilient support element 50. FIG. 13 also shows two layers of the flexible polymer circuit strip 24, a layer 72 including the circuit traces 66 (layer 72 shown in each of FIGS. 9 and 10) and a layer 74 including the contact pad 28 and the strip electrodes 26 (layer 74 shown in FIG. 10). The contact pad 28 shown in FIG. 13 is wider than the surface mountable electrode 38. In some embodiments, the contact pad 28 may be narrower or the same width as the surface mountable electrode 38. The surface mountable electrode 38 is electrically connected to the contact pad 28 using at least one electrically conductive retainer 68. In some embodiments, the proximal end and the distal end of the surface mountable electrode 38 is electrically connected to the contact pad 28 using two respective electrically conductive retainers 68. The proximal end and the distal end of the surface mountable electrode 38 is optionally connected to the flexible polymer circuit strips 24 using adhesive 70. The adhesive 70 typically covers the remainder of the contact pad 28 that is not covered by the surface mountable electrode 38. The adhesive 70 may comprise polyurethane adhesive or epoxy, by way of example. While the bonds 68 are typically disposed on the outer surface of the flexible polymer circuit strip 24, the adhesive 70 is generally disposed around the flexible polymer circuit strip 24 and the elongated resilient support element 50 so as to secure the surface mountable electrode 38 to the flexible polymer circuit strip 24 and the elongated resilient support element 50 and prevent liquid contacting the contact pad 28 in use of the catheter 12.

Figure 14:
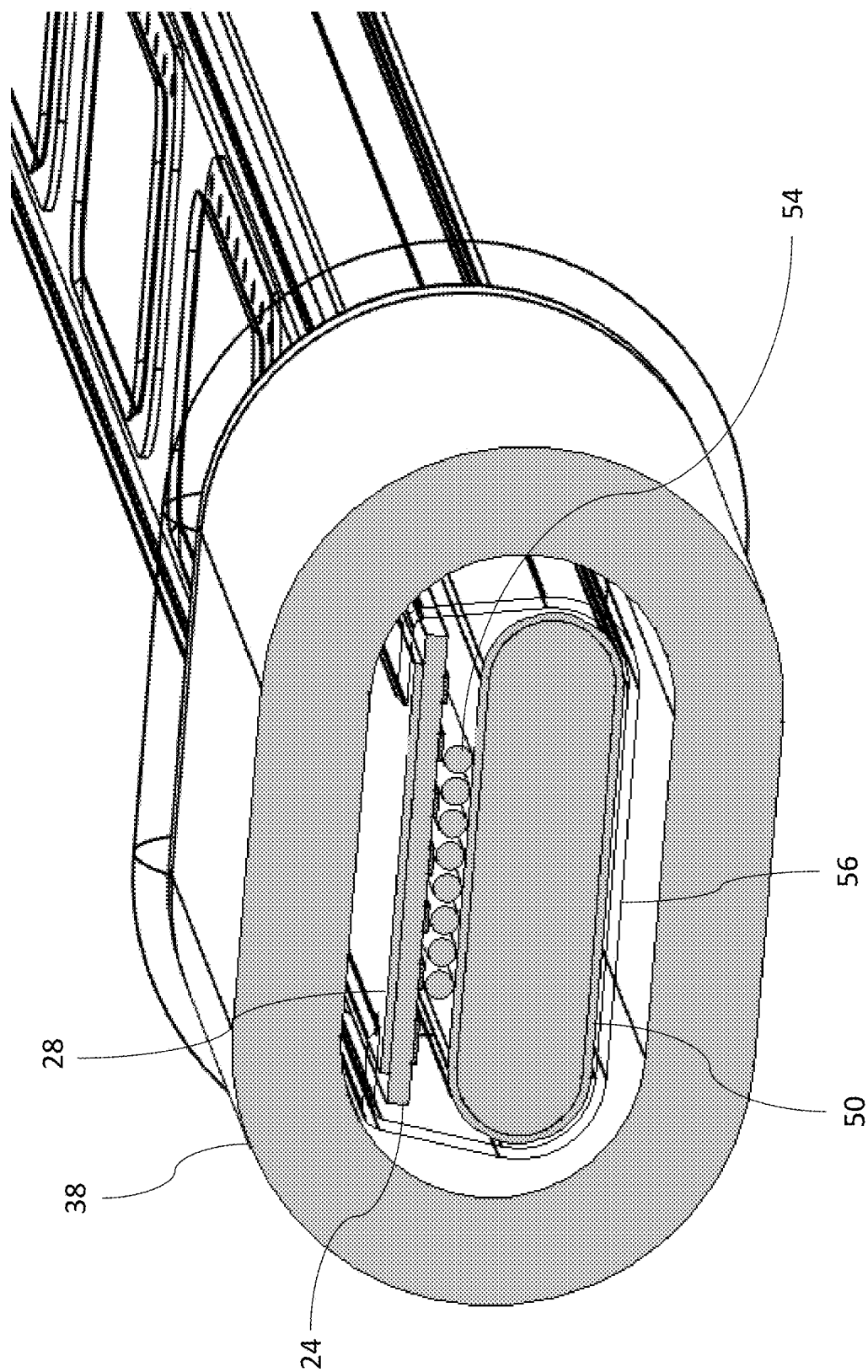
FIG. 14 is a cross-sectional view through line B:B of FIG. 12.

Reference is now made to FIG. 14, which is a cross-sectional view through line B:B of FIG. 12. FIG. 14 shows that the surface mountable electrode 38 extends around the flexible polymer circuit strip 24 and the elongated resilient support element 50. FIG. 14 also shows the yarn 54 sandwiched between the flexible polymer circuit strip 24 and the elongated resilient support element 50. The covering 56 (e.g., shrink-sleeves) is shown surrounding the elongated resilient support elements 50 and partially surrounding the flexible polymer circuit strips 24 where a window is opened in the covering 56 to expose the contact pad 28. The surface mountable electrode 38 shown in FIG. 14 is a one-piece hollowed electrode which is slid over the flexible polymer circuit strip 24 and elongated resilient support element 50 combination. As previously mentioned, the surface mountable electrode 38 may be formed from two halves which are connected together around strip 24. In yet other embodiments, the surface mountable electrode 38 may be formed as a band, which is wrapped around the flexible polymer circuit strip 24.

Figure 15:
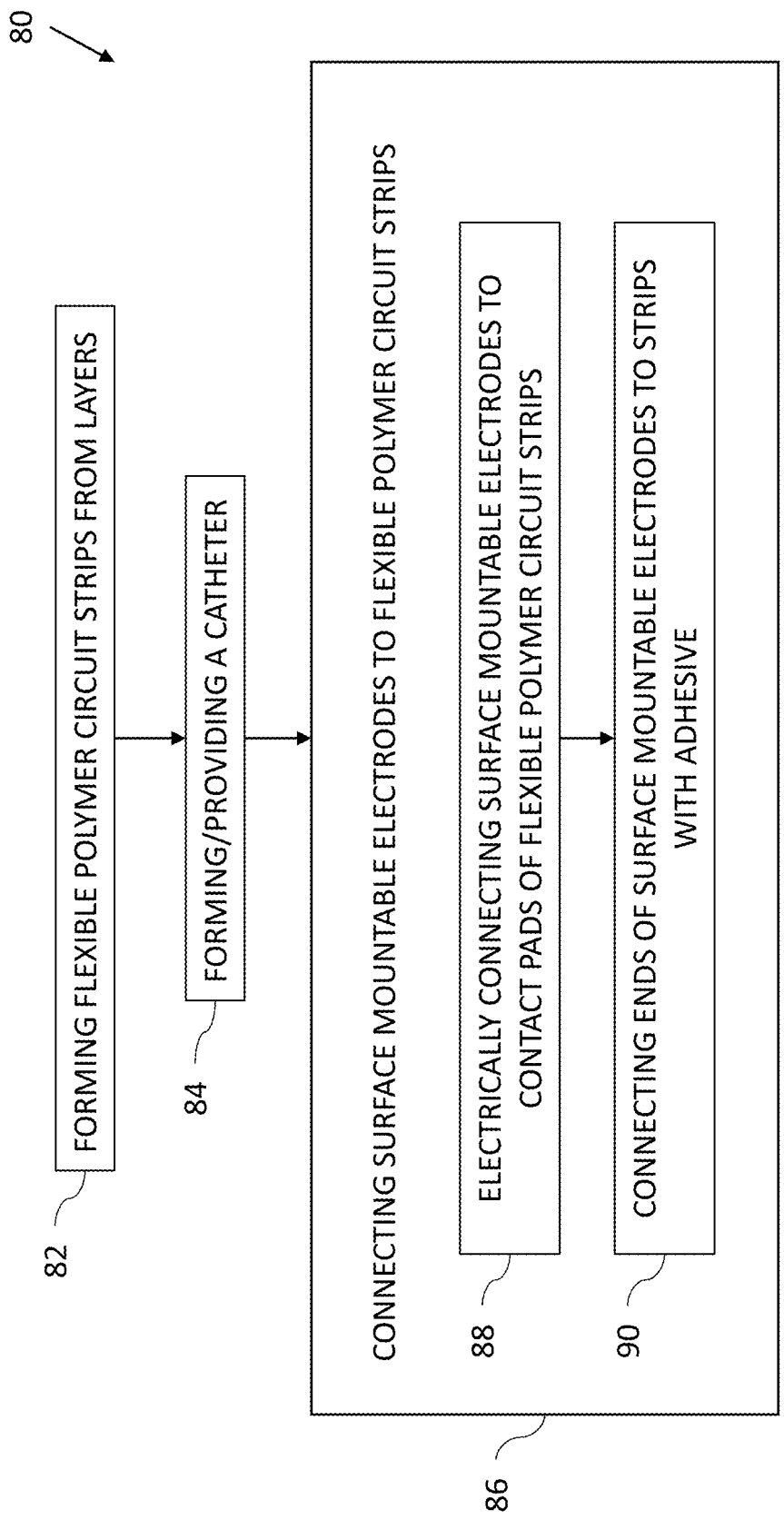
FIG. 15 is a flowchart including steps in a method of manufacturing the catheter of FIG. 2.

Reference is now made to FIG. 15, which is a flowchart 80 including steps in a method of manufacturing the catheter 12 of FIG. 2. Reference is also made to FIG. 1.

The method includes forming (block 82) each flexible polymer circuit strip 24 from multiple layers, with the layer 72 (FIG. 13) comprising circuit traces 66 (FIGS. 9 and 10) and the layer 74 (FIG. 13) including the strip electrodes 26 and the respective contact pad 28.

The method includes forming or providing (block 84) the catheter 12 including: the elongated deflectable element 16; the proximal coupler 20 connected to the distal end 18 of the deflectable element 16; the distal coupler 34; the distal electrode 36; the pusher 30; and the expandable assembly 22. The expandable assembly 22 includes the flexible polymer circuit strips 24. Each flexible polymer circuit strip 24 includes the respective strip electrodes 26 and the respective contact pad 28 disposed thereon. The proximal ends and distal ends of the flexible polymer circuit strips 24 are connected to, and disposed circumferentially around, the proximal coupler 20 and the distal coupler 34, respectively. The distal electrode 36 is disposed at the distal tip of the catheter 12 between the distal ends of the flexible polymer circuit strips 24. The pusher 30 is configured to be advanced and retracted through the deflectable element 16. The distal portion of the pusher 30 is connected to the distal coupler 34. The flexible polymer circuit strips 24 are disposed circumferentially around the distal portion of the pusher 30. The flexible polymer circuit strips 24 are configured to bow radially outward when the pusher 30 is retracted expanding the expandable assembly 22 from a collapsed form to an expanded form.

The method also includes connecting (block 86) the surface mountable electrodes 38 to respective ones of the flexible polymer circuit strips 24. In some embodiments, the method includes connecting the surface mountable electrodes 38 to respective ones of the flexible polymer circuit strips 24 in a staggered formation with alternate ones of the surface mountable electrodes 38 being disposed more proximally that other ones of the surface mountable electrodes 38. The step of block 86 may include the sub-steps of blocks 88 and 90 as follows.

The method may also include electrically connecting (block 88) the surface mountable electrodes 38 to respective ones of the flexible polymer circuit strips 24 so that each surface mountable electrode 38 is electrically connected to the respective contact pad 28 of a respective one of the flexible polymer circuit strips 24 using at least one electrically conductive retainer 68 (FIG. 13), for example, using solder, conductive epoxy, resistance welding, laser welding, or any other suitable method. In some embodiments, the method includes electrically connecting the proximal and distal end of each surface mountable electrode 38 to the respective contact pad 28 of the respective flexible polymer circuit strip 24 using two respective electrically conductive retainers 68.

The method may also include connecting (block 90) the proximal and distal end of each surface mountable electrode 38 to the respective flexible polymer circuit strip 24 using adhesive 70.

Figure 16:
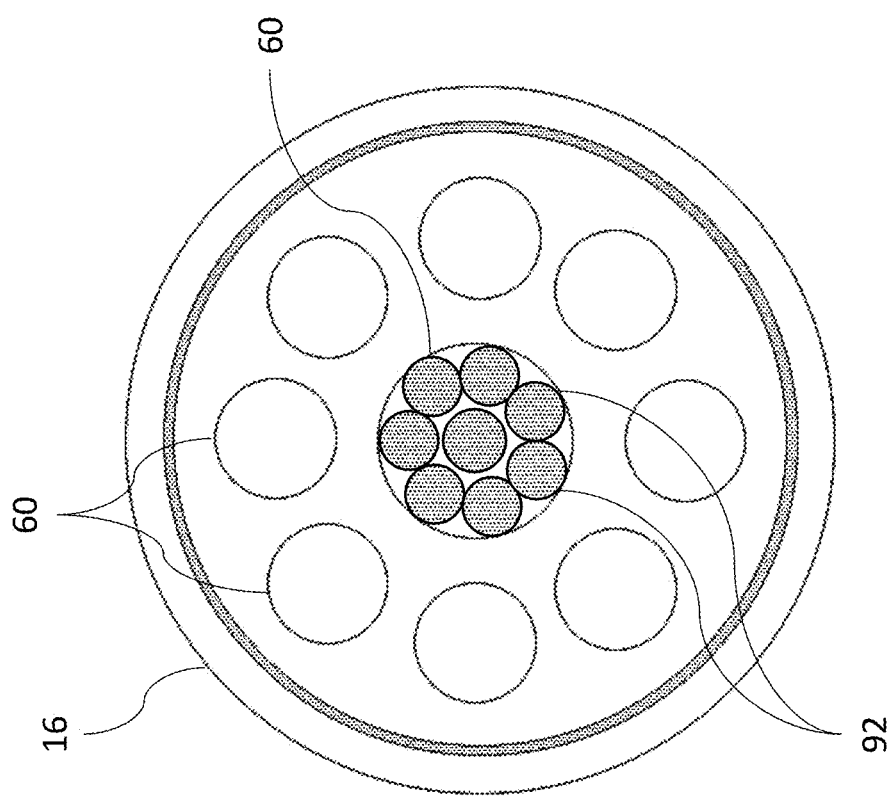
FIG. 16 is an axial cross-sectional view of an elongated deflectable element of the catheter of FIG. 2.

Reference is now made to FIG. 16, which is an axial cross-sectional view of the deflectable element 16 of the catheter 12 of FIG. 1. The deflectable element 16 includes lumens 60 (only some labeled for the sake of simplicity) disposed therein. The lumens 60 may be used to carry cables 92 (only some labeled for the sake of simplicity) therein, and/or other elements such as deflection wires, stiffening elements to create a deflection plane of the deflectable element 16, and a puller wire or the pusher 30 (FIG. 2). The cables 92 are shown disposed in the central lumen 60. The cables 92 may be disposed in one or more non-central lumens 60 in addition to, or instead of, being disposed in the central lumen 60.

Figure 17:
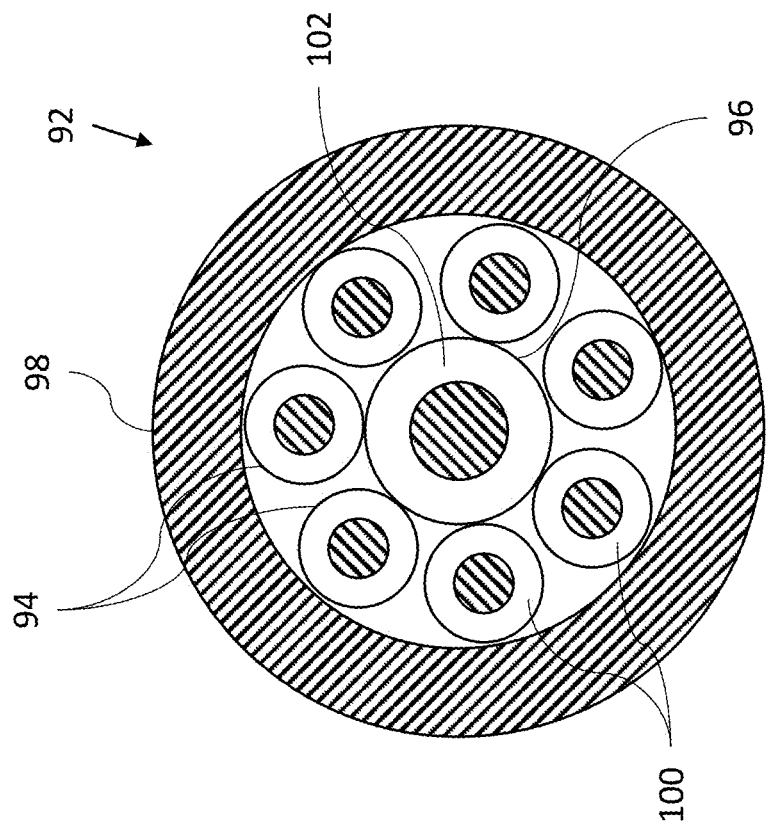
FIG. 17 is an axial cross-sectional view of cable disposed in the elongated deflectable element of FIG. 16.

Reference is now made to FIG. 17, which is an axial cross-sectional view of one of the cables 92 of FIG. 16. The strip electrodes 26 (FIG. 1) and the surface mountable electrodes 38 (FIG. 1) are electrically connected to the proximal end of the catheter 12 (FIG. 1) and the processor 44 (FIG. 1) and the ablation power generator 40 (FIG. 1), respectively, via insulated electrical wires 94 and insulated electrical wires 96. In other words, the strip electrodes 26 are electrically connected via the insulated electrical wires 94 and the surface mountable electrodes 38 are electrically connected via the insulated electrical wires 96. The insulated electrical wires 94 and the insulated electrical wires 96 are disposed in the cables 92 in the lumen(s) 60 (FIG. 16) of the deflectable element 16 (FIG. 16).

In some embodiments, the insulated electrical wires 94 and the insulated electrical wires 96 are disposed in the cables 92 using respective cable jackets 98 so that the cable jackets 98 are disposed in the deflectable element 16. In some embodiments, as shown in FIG. 17, several insulated electrical wires 94 are disposed in one of the cable jackets 98 with one of the insulated electrical wires 96. In general, respective groups of the insulated electrical wires 94 (e.g., grouped by the flexible polymer circuit strips 24 that the insulated electrical wires 94 are connected to) are disposed in respective ones of the cable jackets 98 (e.g., using an extruded tube of Perfluoroalkoxy alkane (PFA)), and respective ones of the insulated electrical wires 96 wires are disposed in respective ones of the cable jackets 98 among the respective groups of the insulated electrical wires 94. For example, the insulated electrical wires 94 and the insulated electrical wires 96 are grouped in the cable jackets 98 according to the flexible polymer circuit strips 24 to which the insulated electrical wires 94 and the insulated electrical wires 96 are electrically connected.

In some embodiments, the wire gauge of each of the insulated electrical wires 94 is greater than the wire gauge of each of the insulated electrical wires 96. The wire gauge of the insulated electrical wires 94 may have any suitable gauge, for example 48 AWG (American Wire Gauge), and may be formed from any suitable conductor, e.g., a copper-silver alloy, which provides extra strength for the thin wires 94. The wire gauge of the insulated electrical wires 96 may have any suitable gauge, for example 42 gauge, and may be formed from any suitable conductor, e.g., copper. The wire gauge of the insulated electrical wires 96 is typically chosen to support the currents supplied to the surface mountable electrodes 38 during IRE or RF ablation.

In some embodiments, the insulation of the insulated electrical wires 96 is thicker than the insulation of the insulated electrical wires 94. The thinner insulation of the insulated electrical wires 94 is generally more difficult to mechanically strip than the insulation of the insulated electrical wires 96.

The insulating material of the insulated electrical wires 94 may be formed from any suitable material, for example, but not limited to, high temperature polyurethane. The insulating material of the insulated electrical wires 96 may be formed from any suitable material, for example, but not limited to, high temperature polyimide.

In order to allow easy connection of the insulated electrical wires 94 to the contact arrays 64 (FIG. 9), the insulated electrical wires 94 include electrically insulating material 100 (only some labeled for the sake of simplicity) which is configured to have a temperature rating between 150 and 200 degrees Centigrade so that the electrically insulating material 100 melts or degrades (e.g., chars and crumbles) during soldering of the insulated electrical wires 94 to the contact arrays 64 (e.g., at a temperature of 300 degrees Centigrade) and therefore insulation of the insulated electrical wires 94 does not need to be mechanically stripped. The electrically insulating material 100 is more difficult to remove than the thicker insulation of the insulated electrical wires 96, when the insulation of the insulated electrical wires 96 is indeed thicker. In some embodiments, the insulated electrical wires 96 also include the electrically insulating material 100 which is configured to have a temperature rating between 150 and 200 so that the electrically insulating material 100 melts during soldering of the insulated electrical wires 96 to the contact arrays 64.

In other embodiments, described in more detail with reference to FIGS. 18-20, the insulated electrical wires 96 include electrically insulating material 102 which is configured to have a temperature rating greater than 200 degrees Centigrade to prevent the electrically insulating material 102 melting or degrading (e.g., charring and crumbling) during manufacture of the catheter 12 and/or during use. The electrically insulating material 102 is generally mechanically stripped before soldering the insulated electrical wires 96 to the surface mountable electrodes 38 as described in more detail below.

Figure 18:
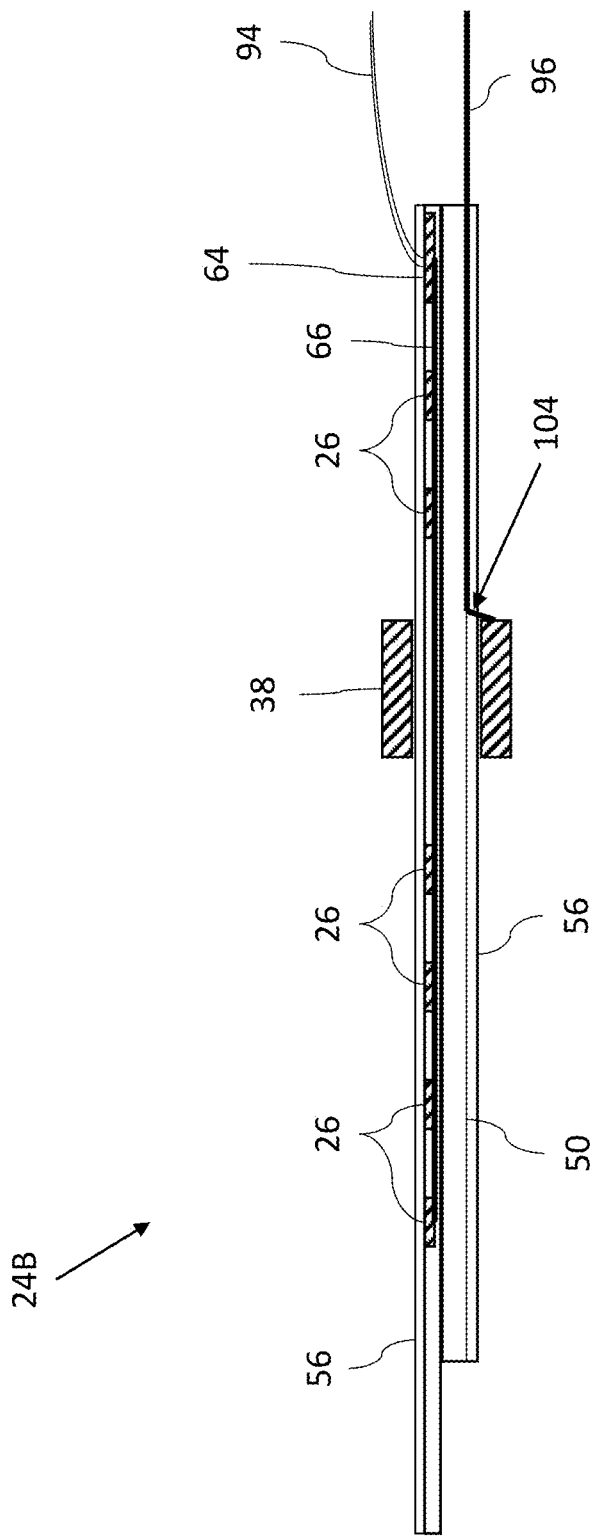
FIG. 18 is a schematic longitudinal cross-sectional view of an alternative flexible polymer circuit strip for use with the catheter of FIG. 2.

Reference is now made to FIG. 18, which is a schematic longitudinal cross-sectional view of an alternative flexible polymer circuit strip 24B for use with the catheter 12 of FIG. 2. In some embodiments, the flexible polymer circuit strips 24 described above with reference to FIGS. 2-15 may be replaced with flexible polymer circuit strips 24B. The flexible polymer circuit strips 24B are substantially the same as the flexible polymer circuit strips 24 except for the differences described herein below.

FIG. 18 shows that the flexible polymer circuit strip 24B includes the multiple strip electrodes 26, the contact array 64 disposed at the proximal end of the flexible polymer circuit strip 24B, multiple circuit traces 66 (shown more clearly in FIGS. 9 and 10) electrically connecting the multiple strip electrodes 26 with the contact array 64, and the elongated resilient support element 50. Therefore, when the flexible polymer circuit strips 24B replace the flexible polymer circuit strips 24, the catheter 12 (FIG. 1) includes respective flexible polymer circuit strips 24B including: respective multiple strip electrodes 26 (i.e., multiple strip electrodes 26 per flexible polymer circuit strip 24B); respective contact arrays 64 disposed at the respective proximal ends (i.e., one contact array 64 disposed at the proximal end of each flexible polymer circuit strip 24B); and respective multiple circuit traces 66 electrically connecting the respective multiple strip electrodes 26 with the respective contact arrays 64 (i.e., the circuit traces 66 of each flexible polymer circuit strip 24B electrically connect the contact array 64 to the strip electrodes 26 of that flexible polymer circuit strip 24B).

The catheter 12 also includes the surface mountable electrodes 38 mounted on and configured such that each electrode 38 can be seen to be bulging over respective ones of the flexible polymer circuit strips 24B. That is, each electrode 38 is disposed in such a way that the flexible circuit strip 24B is interposed into a hollow body portion such that the electrode 38 appears to be bulging or protruding from strip 24B such as seen in FIGS. 7A and 11. For example, each of the flexible polymer circuit strips 24B may include one of the surface mountable electrodes 38 mounted thereon. As used herein, the terms "bulge", "bulging", "protrude", "protruding", "interpose" or "interposing" are used interchangeably to indicate the physical configuration of the larger electrode 38 disposed with respect to smaller strip 24B extending through larger electrode 38 along a central axis of electrode 38 such that larger electrode 38 appears to be bulging from strip 24B.

The respective groups of the insulated electrical wires 94 are electrically connected to the respective contact arrays 64 of respective ones of the flexible polymer circuit strips 24B. FIG. 18 shows one group of the insulated electrical wires 94 electrically connected to the flexible polymer circuit strip 24B of FIG. 18. Respective ones of the insulated electrical wires 96 are run externally to respective ones of the flexible polymer circuit strips 24B and are electrically connected to respective ones of the surface mountable electrodes 38. FIG. 18 shows one of the insulated electrical wires 96 running externally to the flexible polymer circuit strip 24B below the elongated resilient support element 50 and electrically connected to the surface mountable electrode 38.

The flexible polymer circuit strips 24B are covered with the coverings 56, e.g., respective shrink-sleeves formed from any suitable material such as PET shrink-tubing. The coverings 56 (e.g., shrink-sleeves) secure respective ones of the insulated electrical wires 96 to respective ones of the flexible polymer circuit strips 24B. FIG. 18 shows one of the insulated electrical wires 96 being secured to the flexible polymer circuit strip 24B via the elongated resilient support element 50. The covering 56 is typically shrunk using heat. Therefore, the electrically insulating material 102 (FIG. 17) of the insulated electrical wires insulated electrical wires 96 needs to be able to withstand the heat applied to the covering 56. If the electrically insulating material 102 melts or degrades, the conductor in the insulated electrical wire 96 may short with the elongated resilient support element 50, which may be formed from a metal such as Nitinol. Windows (not shown) are cut in the covering 56 above the strip electrodes 26 and the contact array 64. FIG. 18 shows the covering 56 prior to cutting the windows. For the sake of simplicity, FIG. 18 does not show the covering 56 at the ends of the flexible polymer circuit strip 24B and the elongated resilient support element 50.

The surface mountable electrode 38 of FIG. 18 is mounted externally to the covering 56 (e.g. shrink-sleeve) of the flexible polymer circuit strip 24B. In general, respective ones of the surface mountable electrodes 38 are mounted externally to the respective coverings 56 (e.g. shrink-sleeves) of respective ones of the flexible polymer circuit strips 24B. The surface mountable electrodes 38 may be affixed to the flexible polymer circuit strips 24B using a pressure fit and/or using a suitable adhesive and/or other securing method.

The insulated electrical wire 96 exits from the covering 56 via a hole 104 in the covering 56. The distal end of the insulated electrical wire 96 is manually stripped (e.g., using a suitable mechanical wire stripper) and is soldered to the surface mountable electrode 38.

The manufacture of the cables 92 and the flexible polymer circuit strips 24B is described in more detail with reference to FIGS. 19 and 20.

Figure 19:
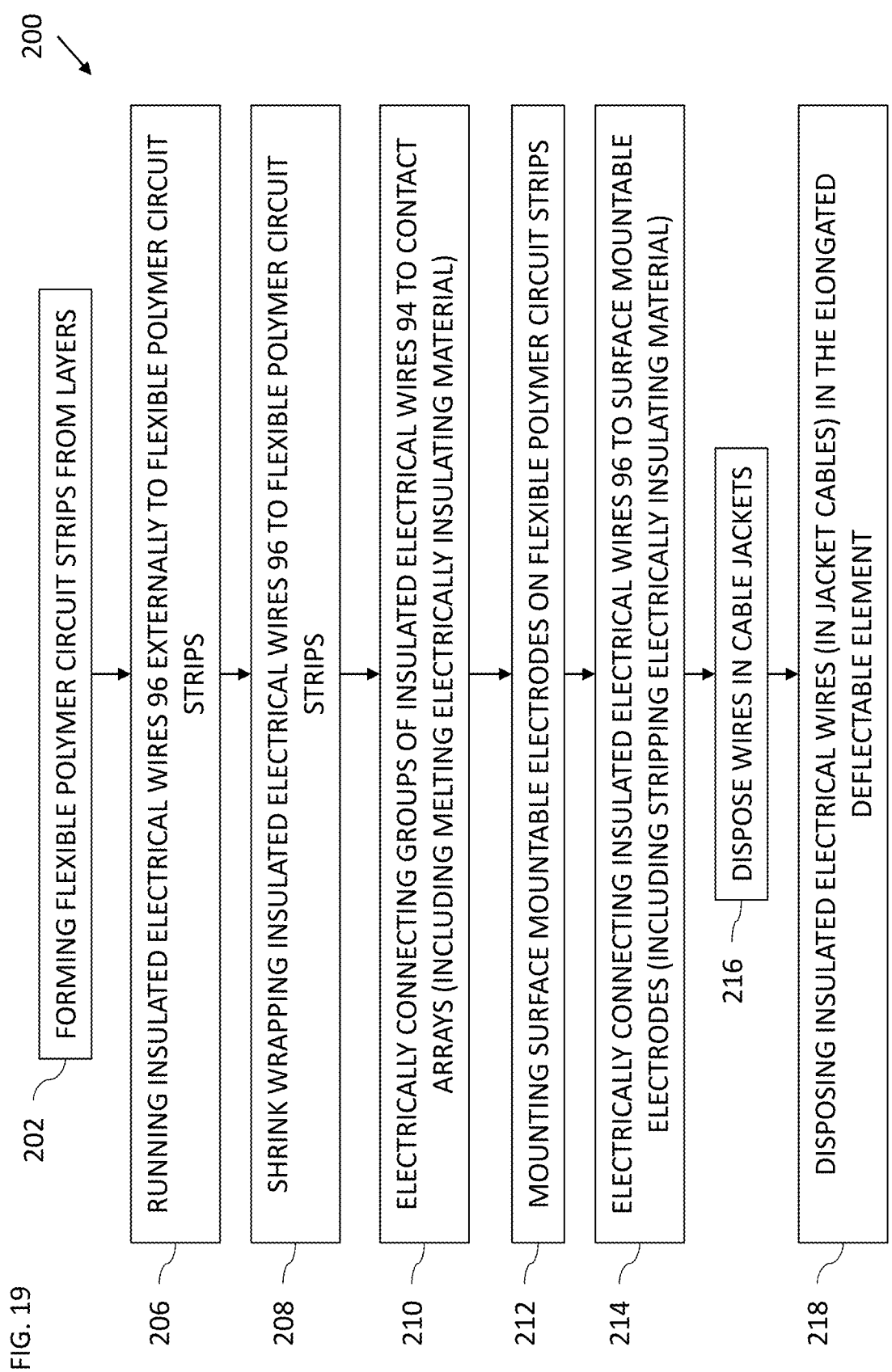
FIG. 19 is a flowchart including steps in a method of manufacture of a catheter including the flexible polymer circuit strip of FIG. 18.

Reference is now made to FIG. 19, which is a flowchart 200 including steps in a method of manufacture of a catheter including the flexible polymer circuit strip 24B of FIG. 18. Reference is also made to FIGS. 17 and 18.

The method includes forming or providing a catheter including: the deflectable element 16 (FIG. 1), the proximal coupler 20 (FIG. 1) connected to the distal end of the elongated deflectable element 16, and the expandable assembly 22 (FIG. 1) including the flexible polymer circuit strips 24B. The flexible polymer circuit strips 24B have respective proximal ends connected to, and disposed circumferentially around, the proximal coupler 20. Respective ones of the flexible polymer circuit strips 24B include: respective multiple strip electrodes 26; respective contact arrays 64 disposed at the respective proximal ends; and respective multiple circuit traces 66 electrically connecting the respective multiple strip electrodes 26 with the respective contact arrays 66. Formation of the flexible polymer circuit strips 24B is described in more detail below.

It should be noted that the steps listed below with reference to FIGS. 19 and 20 may be performed in any suitable order and not just the order described below. The method includes forming (block 202) the flexible polymer circuit strips 24B from layers as described above with reference to FIGS. 9 and 10. The method also includes running (block 206) respective ones of the insulated electrical wires 96 externally to respective flexible polymer circuit strips 24B and shrink-wrapping (block 208) respective ones of the insulated electrical wires 96 to respective ones of the flexible polymer circuit strips 24B. This step is generally performed in two stages as described in more detail with reference to FIG. 20. The method may also include cutting windows in the coverings 56 (e.g., shrink-sleeves) for the strip electrodes 26 and the contact arrays 64.

The method includes electrically connecting (block 210) (e.g., using soldering) respective groups of the insulated electrical wires 94 to the respective contact arrays 64 of respective ones of the flexible polymer circuit strips 24B. The electrically connecting of the step of block 210 may also include melting or degrading (e.g., from the heat of the soldering process) the electrically insulating material 100 of the insulated electrical wires 94 at the regions where the insulated electrical wires 94 join the contact arrays 64.

The method also includes mounting (block 212) the surface mountable electrodes 38 over respective ones of the flexible polymer circuit strips 24B with the surface mountable electrodes 38 bulging over the respective flexible polymer circuit strips 24B. The step of block 212 may also include sliding the surface mountable electrodes 38 over the coverings 56 (e.g., shrink-sleeves) of the respective flexible polymer circuit strips 24B.

The method also includes electrically connecting (block 214) (e.g., using soldering) respective ones of the insulated electrical wires 96 to respective ones of the surface mountable electrodes 38. The step of block 214 may include mechanically stripping the electrically insulating material 102 of the distal ends of the insulated electrical wires 96 prior to electrically bonding the insulated electrical wires 96 to the surface mountable electrodes 38.

The method also includes disposing (block 216) the respective groups of the insulated electrical wires 94 and respective ones of the insulated electrical wires 96 in respective ones of the cable jackets 98 of the respective cables 92. The step of block 216 may include disposing respective ones of the insulated electrical wires 96 in respective ones of the cable jackets 98 (i.e., one insulated electrical wire 96 per cable jacket 98) among the respective groups of the insulated electrical wires 94 (i.e., multiple insulated electrical wires 94 per cable jacket 98). In some embodiments, the insulated electrical wires 94 and the insulated electrical wires 96 are grouped according to their connections with the flexible polymer circuit strips 24B so that if the catheter 12 includes 8 flexible polymer circuit strips 24B, the catheter 12 also includes 8 corresponding cables 92 with cable jackets 98. The cable jackets 98 may be formed by extruding a tube (e.g., of PFA) over each wire bundle.

The method also includes disposing (block 218) the insulated electrical wires 94 and the insulated electrical wires 96 (which may be disposed in the cable jackets 98 of the cables 92) in the lumen(s) 60 (FIG. 16) of the deflectable element 16 (FIG. 16).

Figure 20:
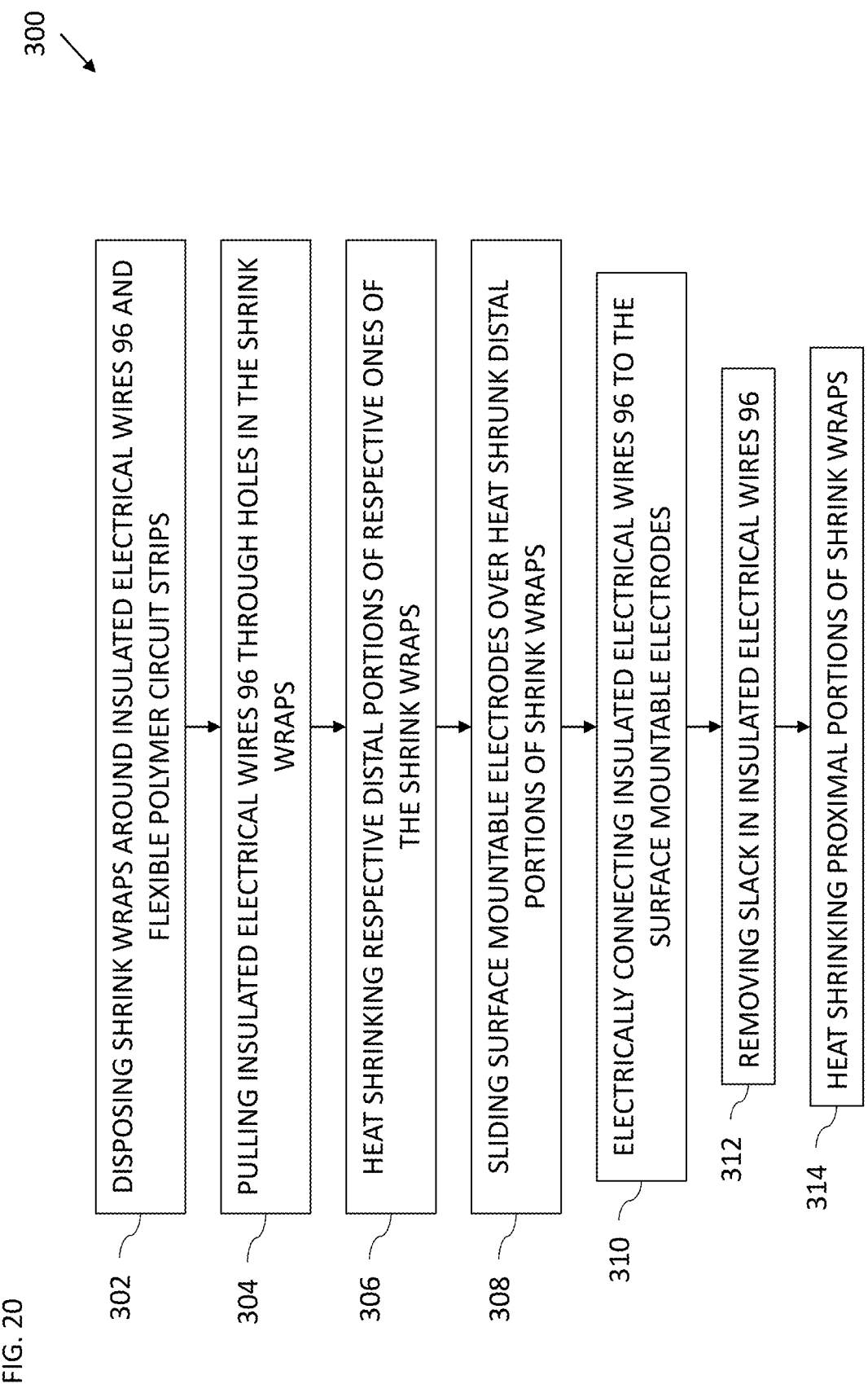
FIG. 20 is a flowchart including more detailed steps in a method of manufacture of a catheter including the flexible polymer circuit strip of FIG. 18.

Reference is now made to FIG. 20, which is a flowchart 300 including more detailed steps in a method of manufacture of a catheter including the flexible polymer circuit strips 24B of FIG. 18.

The method includes disposing (block 302) respective coverings 56 (e.g., shrink-sleeves) around respective ones of the insulated electrical wires 96 and flexible polymer circuit strips 24B. The respective coverings 56 typically cover all sides of the respective flexible polymer circuit strips 24B including the respective elongated resilient support elements 50.

The method includes forming holes 104 in the coverings 56 (proximal to where the respective surface mountable electrodes 38 will be disposed on the respective flexible polymer circuit strips 24B), and pulling (block 304) respective distal ends of the insulated electrical wires 96 through the respective holes 104 in the respective coverings 56 (e.g., shrink-sleeves). The method also includes heat shrinking (block 306) respective distal portions (i.e., distal of the holes 104) of respective ones of the coverings 56 (e.g., shrink-sleeves).

The method includes sliding (block 308) respective ones of the surface mountable electrodes 38 over the heat shrunk distal portions of respective ones of the coverings 56 (e.g., shrink-sleeves) and electrically connecting (block 310) the distal ends of the respective insulated electrical wires 96 to respective ones of the surface mountable electrodes 38.

The method also includes removing slack (block 312) in respective ones of the insulated electrical wires 96, for example, by pulling the proximal ends of the insulated electrical wires 96. The method also includes heat shrinking (block 314) proximal portions (i.e., proximal of the holes 104) of respective ones of the coverings 56 (e.g., shrink-sleeves). The heat shrinking is performed in two stages as described above so that slack may be removed from the insulated electrical wires 96 after the insulated electrical wires 96 are connected to the surface mountable electrodes 38 which is after the surface mountable electrodes 38 are mounted on the distal end of the heat shrunk coverings 56.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A medical system including a catheter configured to be inserted into a body part of a living subject, and comprising:
    an elongated deflectable element including a distal end;
    a proximal coupler connected to the distal end;
    an expandable assembly comprising a plurality of flexible polymer circuit strips, the flexible polymer circuit strips having respective proximal ends connected to, and disposed circumferentially around, the proximal coupler, respective ones of the flexible polymer circuit strips including: respective multiple strip electrodes; respective contact arrays disposed at the respective proximal ends; and respective multiple circuit traces electrically connecting the respective multiple strip electrodes with the respective contact arrays; and
    a plurality of surface mountable electrodes mounted on, and bulging over respective ones of the flexible polymer circuit strips such that each flexible polymer circuit strip extends through respective ones of the surface mountable electrodes, wherein the plurality of surface mountable electrodes are configured to ablate a tissue of the body part.

2. The system according to claim 1, wherein the catheter further comprises:
    first insulated electrical wires disposed in the elongated deflectable element, respective groups of the first insulated electrical wires being electrically connected to the respective contact arrays of respective ones of the flexible polymer circuit strips; and
    second insulated electrical wires disposed in the elongated deflectable element, respective ones of the second insulated electrical wires being run externally to respective ones of the flexible polymer circuit strips and being electrically connected to respective ones of the surface mountable electrodes.

3. The system according to claim 2, wherein:
    the first insulated electrical wires include electrically insulating material which is configured to have a temperature rating between 150 and 200 degrees Centigrade; and
    the second insulated electrical wires include electrically insulating material which is configured to have a temperature rating greater than 200 degrees Centigrade.

4. The system according to claim 3, wherein:
    respective ones of the first insulated electrical wires have a first wire gauge;
    respective ones of the second insulated electrical wires have a second wire gauge; and the first wire gauge is greater than the second wire gauge.

5. The system according to claim 3, wherein the catheter includes respective shrink-sleeves securing respective ones of the second wires to respective ones of the flexible polymer circuit strips.

6. The system according to claim 5, wherein respective ones of the surface mountable electrodes are mounted externally to the respective shrink-sleeves of respective ones of the flexible polymer circuit strips.

7. The system according to claim 2, wherein:
    the catheter includes respective cable jackets disposed in the elongated deflectable element;
    the respective groups of the first insulated electrical wires are disposed in respective ones of the cable jackets; and
    respective ones of the second insulated electrical wires are disposed in respective ones of the cable jackets among the respective groups of the first insulated wires.

8. The system according to claim 1, wherein each respective one of the surface mountable electrodes extends around the respective flexible polymer circuit strip.

9. The system according to claim 1, further comprising:
    an ablation power generator configured to be connected to the catheter, and apply an electrical signal to at least one of the surface mountable electrodes to ablate a tissue of the body part; and
    a mapping module configured to: receive electrical signals from ones of the strip electrodes of the flexible polymer circuit strips; and generate an electro-anatomical map responsively to the received electrical signals.

10. The system according to claim 1, wherein:
    the catheter includes a pusher including a distal portion, and being configured to be advanced and retracted through the deflectable element;
    the catheter includes a distal coupler connected to the distal portion of the pusher; and the flexible polymer circuit strips are disposed circumferentially around the distal portion of the pusher;
    the flexible polymer circuit strips have respective distal ends connected to the distal coupler; and
    the strips being configured to bow radially outward when the pusher is retracted expanding the expandable assembly from a collapsed form to an expanded form.

11. The system according to claim 1, wherein the surface mountable electrodes are configured to ablate the tissue of the body part using radio frequency or irreversible electroporation ablation.

12. A catheter device configured to be inserted into a body part of a living subject, and comprising:
    an elongated deflectable element including a distal end;
    a distal end assembly disposed at the distal end and comprising a plurality of first electrodes and a plurality of second electrodes;
    first insulated electrical wires disposed in the elongated deflectable element, respective ones of the first insulated electrical wires being electrically connected via solder to respective ones of the first electrodes, the first insulated electrical wires including first electrically insulating material which is configured to have a temperature rating between 150 and 200 Centigrade such that an end portion of the first electrically insulating material is melted or degraded after the solder is applied; and second insulated electrical wires disposed in the elongated deflectable element, respective ones of the second insulated electrical wires being electrically connected to respective ones of the second electrodes, the second electrodes being configured to ablate a tissue of a body part, the second insulated electrical wires including electrically insulating material which is configured to have a temperature rating greater than 200 degrees Centigrade.

13. The device according to claim 12, further comprising shrink-sleeves covering at least part of the second insulated electrical wires.

14. A method of manufacturing a catheter comprising:
providing a catheter including an elongated deflectable element, a proximal coupler connected to a distal end of the elongated deflectable element, and an expandable assembly comprising a plurality of flexible polymer circuit strips, the flexible polymer circuit strips having respective proximal ends connected to, and disposed circumferentially around, the proximal coupler, respective ones of the flexible polymer circuit strips including: respective multiple strip electrodes; respective contact arrays disposed at the respective proximal ends; and respective multiple circuit traces electrically connecting the respective multiple strip electrodes with the respective contact arrays; and
mounting a plurality of surface mountable electrodes over respective ones of the flexible polymer circuit strips with the surface mountable electrodes bulging over the respective ones of the flexible polymer circuit strips such that each flexible polymer circuit strip extends through respective ones of the surface mountable electrodes, wherein the plurality of surface mountable electrodes are configured to ablate a tissue of a body part.

15. The method according to claim 14, further comprising:
disposing first insulated electrical wires in the elongated deflectable element;
electrically connecting respective groups of the first insulated electrical wires to the respective contact arrays of respective ones of the flexible polymer circuit strips;
disposing second insulated electrical wires in the elongated deflectable element;
running respective ones of the second insulated electrical wires externally to respective one of the flexible polymer circuit strips; and
electrically connecting respective ones of the second insulated electrical wires to respective ones of the surface mountable electrodes.

16. The method according to claim 15, wherein:
the electrically connecting respective groups of the first insulated electrical wires includes melting electrically insulating material of the first wires; and
the electrically connecting respective ones of the second insulated electrical wires includes mechanically stripping electrically insulating material of the second insulated electrical wires.

17. The method according to claim 16, wherein:
respective ones of the first insulated electrical wires have a first wire gauge;
respective ones of the second insulated electrical wires have a second wire gauge; and
the first wire gauge is greater than the second wire gauge.

18. The method according to claim 16, further comprising shrink-wrapping respective ones of the second insulated electrical wires to respective ones of the flexible polymer circuit strips.

19. The method according to claim 18, further comprising:
disposing respective shrink-sleeves around respective ones of the second insulated electrical wires and respective ones of the flexible polymer circuit strips;
pulling respective ones of the second insulated electrical wires through respective holes in respective ones of the shrink-sleeves;
heat shrinking respective distal portions of respective ones of the shrink-sleeves; sliding respective ones of the surface mountable electrodes over the respective heat shrunk distal portions of respective ones of the shrink-sleeves;
electrically connecting respective ones of the second insulated electrical wires to respective ones of the surface mountable electrodes;
removing slack in respective ones of the second insulated electrical wires; and
heat shrinking respective proximal portions of respective ones of the shrink-sleeves.

20. The method according to claim 15, further comprising:
disposing the respective groups of the first insulated electrical wires in respective cable jackets; and
disposing respective ones of the second insulated electrical wires in respective ones of the cable jackets among the respective groups of the first insulated wires.

21. The method according to claim 14, wherein the surface mountable electrodes are configured to ablate the tissue of the body part using radio frequency or irreversible electroporation ablation.

\* \* \* \* \*